(12) United States Patent
Pincus et al.

(10) Patent No.: US 11,059,882 B2
(45) Date of Patent: *Jul. 13, 2021

(54) ANTI-HIV DUAL SPECIFICITY ANTIBODIES AND METHODS OF HIV TREATMENT

(71) Applicant: Board of Supervisors of Louisiana State University and Agricultural and Mechanical College, Baton Rouge, LA (US)

(72) Inventors: Seth Pincus, New Orleans, LA (US); Ryan Craig, Baton Rouge, LA (US)

(73) Assignee: Board Of Supervisors Of Louisiana State University And Agricultural And Mechanical College, Baton Rouge, LA (US)

( * ) Notice: Subject to any disclaimer, the term of this patent is extended or adjusted under 35 U.S.C. 154(b) by 263 days.

This patent is subject to a terminal disclaimer.

(21) Appl. No.: 15/968,090

(22) Filed: May 1, 2018

(65) Prior Publication Data
US 2018/0251530 A1 Sep. 6, 2018

Related U.S. Application Data

(63) Continuation of application No. 14/907,360, filed as application No. PCT/US2014/047787 on Jul. 23, 2014, now Pat. No. 9,988,438.

(60) Provisional application No. 61/858,149, filed on Jul. 25, 2013.

(51) Int. Cl.
| | |
|---|---|
| *A61K 39/00* | (2006.01) |
| *C07K 16/28* | (2006.01) |
| *C07K 16/10* | (2006.01) |
| *A61K 39/395* | (2006.01) |
| *A61K 45/06* | (2006.01) |
| *C07K 16/46* | (2006.01) |
| *A61K 38/17* | (2006.01) |

(52) U.S. Cl.
CPC ...... *C07K 16/1063* (2013.01); *A61K 38/1774* (2013.01); *C07K 16/468* (2013.01); *A61K 2039/505* (2013.01); *C07K 2317/31* (2013.01); *C07K 2317/70* (2013.01); *C07K 2317/76* (2013.01)

(58) Field of Classification Search
CPC .......... A61K 2039/505; C07K 2317/76; C07K 2317/622; A61P 31/18; A61P 35/00
See application file for complete search history.

(56) References Cited

PUBLICATIONS

International Search Report for PCT/US2014/047787 dated Jan. 15, 2015.
Craig, et al., "Anti-HIV Double Variable Domain Immunoglobulins Binding Both gp41 and gp120 for Targeted Delivery of Immunoconjugates", PLOS ONE, www.plosone.org, Oct. 2012, vol. 7, Issue 10, e46778, 13 pages.
West, et al., "Evaluation of CD4-CD4i Antibody Architectures Yields Potent, Broadly Cross-Reactive Anti-Human Immunodeficiency Virus Reagents", Journal of Virology, Jan. 2010, vol. 84, No. 1, pp. 261-269.
Allaway, et al., "Expression and Characterization of CD4-IgG2, a Novel Heterotetramer That Neutralizes Primary HIV Type 1 Isolates", Aids Research and Human Retroviruses, vol. 11, No. 5, 1995, Mary Ann Liebert, Inc., Publishers, pp. 533-539.
Mouquet, et al., "Enhanced HIV-1 neutralization by antibody heteroligation", PNAS, www.pnas.org/cgi/doi/10.1073/pnas.1120059109, Jan. 17, 2012, vol. 109, No. 3, pp. 875-880.
Zhang, et al., "Identification and Characterization of a Broadly Cross-Reactive HIV-1 Human Monoclonal Antibody That Binds to Both gp120 and gp41", PLOS One, Sep. 2012, vol. 7, Issue 9, 14 pages.
Moebius et al. The Human Immunodeficiency Virus gpl20 Binding Site on CD4: Delineation by Quantitative Equilibrium and Kinetic Binding Studies of Mutants in Conjunction with a High-Resolution CD4 Atomic Structure. Appl. Expt. Med. 1992; 176: 507-517.
G. Gutman, Immunology Core Notes, Medical Immunology 544 (Fall 2011 ), School of Medicine, University of California, Irvine—downloaded Jun. 8, 2017 from http://jeeves.mmg.uci.edu/immunology/CoreNotes/CoreNotes.htm.

*Primary Examiner* — Barry A Chestnut
(74) *Attorney, Agent, or Firm* — Baker Donelson

(57) ABSTRACT

Dual variable domain immunoglobulins (DVD Igs) are provided capable of tetravalent binding to bispecific sites of the human immunodeficiency virus (HIV). The DVD Igs may be asymmetric and may have more variable domains on either the light chain or the heavy chain of the Igs. The DVD Igs may have specificity for gp41 and gp120. Therapies are provided using DVD Igs to neutralize HIV viral loads.

19 Claims, 7 Drawing Sheets

Specification includes a Sequence Listing.

ANTI-HIV DUAL SPECIFICITY ANTIBODIES AND METHODS OF HIV TREATMENT

CROSS-REFERENCE TO RELATED APPLICATIONS

This application is a continuation of, and claims priority to, co-pending U.S. patent application Ser. No. 14/907,360, filed on Jan. 25, 2016, which is incorporated by reference in its entirety. This application also claims priority to and benefit of PCT Application No. PCT/US2014/047787, filed Jul. 23, 2014, which claims benefit of U.S. Provisional Application 61/858,149 filed Jul. 25, 2013, both of which are incorporated herein by reference in their entireties.

INCORPORATION OF SEQUENCE LISTING

The instant application contains a sequence listing which has been submitted with the instant application via EFS-Web. The sequence listing file is named 222271030_ST25.txt and is herein incorporated by reference. The support for the sequences can be found throughout the specification.

FIELD

The present invention relates generally to anti-HIV antibodies and antibody-like molecules and, in particular though non-limiting embodiments, to double-variable domain antibodies and methods of treating an HIV infection.

BACKGROUND

The lentivirus human immunodeficiency virus (HIV) causes Acquired Immunodeficiency Syndrome (AIDS), a condition in humans in which progressive failure of the immune system allows life-threatening opportunistic infections and cancers to thrive. HIV/AIDS is a global pandemic, with most recent World Health Organization studies estimating nearly 34 million people are infected with HIV. This figure includes over 3 million children under the age of 15. Currently, no cure for HIV exists.

The HIV virus infects a large number of different cells in the body, including various cell types of the immune system, but its infection of CD4 T-lymphocytes largely underlies HIV pathogenesis. HIV-infection leads to reduced CD4 T-lymphocytes, further leading to progressive loss of cell-mediated immunity and an increased susceptibility to opportunistic infections.

The HIV virus consists of a viral envelope enclosing a capsid, which itself encloses the viral genome. The HIV envelope protein (Env) consists of precursor gp160 of the transmembrane domain gp41 (e.g., SEQ ID NO 1, which is one of many sequences for gp41) and the external domain gp120 (e.g. SEQ ID NO 2, which is one of many sequences for gp120), which are involved in virus-cell attachment. Mechanistically, gp120 attaches to the CD4 molecule present on T-lymphocytes, a series of conformational changes occur with gp120 and gp41, and gp41 mediates the fusion of the viral and cellular membranes and insertion of viral core and the genomic material into the target cell, resulting in host cell infection.

Conventional neutralizing antibodies generally consist of two identical heavy chains and two identical light chains, each with a single variable domain ($V_H$ or $V_L$) at the N-termini of the molecule. More recently, neutralizing antibodies have been adapted to include a second variable region connected via a linker (L) sequence at the N-termini of the variable domains of a conventional molecule and are generally referred to as a dual variable domain immunoglobulins (DVD-Igs). DVD-Igs are immunoglobulin-derived molecules that contain two unique variable domains (V domains) linked to a constant region with the capability of tetravalent, bispecific binding, while retaining affinity and specificity of each of the parental antibodies. For example, DVD-Igs have been constructed that can bind both IL1a and IL1b, or IL-12 and IL-18. DVD-Igs have been proven effective in vitro and in vivo, and retain pharmacokinetic properties of the parental antibodies.

The idea of targeting two separate antigenic sites with a single antibody has also been directed against HIV. The most common approach has been to construct dual domain antibodies using an anti-gp120 V-region fused to CD4. When the inter-domain linker length was optimized, enhanced neutralization by these CD4-anti-gp120 immunoadhesins was obtained. Bi-specific antibodies with one V-domain against gp41 and one against gp120 have been produced; however the antibodies do not neutralize the virus as well as embodiments of the present invention. The failure to make effective neutralizing antibodies is due in part to the enormous sequence diversity of HIV-1, and the relative inaccessibility of conserved domains of the HIV virus.

Accordingly, there is need for novel antibodies and antibody like molecules and methods of neutralizing and eradicating HIV.

SUMMARY

In an exemplary embodiment of the present invention, an antibody is provided, including: at least one variable domain with binding affinity to HIV gp120 and at least one variable domain with binding affinity to HIV gp41. At least one of a heavy chain and a light chain of the antibody has a variable domain with binding affinity to HIV gp120 linked by a linker to a variable domain with binding affinity to HIV gp41. In certain embodiments, only one of the heavy chain and the light chain may have two variable domains. In certain embodiments, both the heavy chain and light chain may have two variable domains.

The linker may be one of a helical linker and a flexible linker. The linker may be one of SEQ ID NO:9 and SEQ ID NO:10. The antibody may include both chains of full-length 7B2 antibody. The heavy chain may have one variable domain with binding affinity to HIV gp41 and the light chain may have a first variable domain with binding affinity to HIV gp120 linked by the linker to a second variable domain with binding affinity to HIV gp41. The light chain may have one variable domain with binding affinity to gp41 and the heavy chain may have a first variable domain with binding affinity to HIV gp120 linked by the linker to a second variable domain with binding affinity to HIV gp41. Both the light chain and the heavy chain may have a first variable domain with binding affinity to HIV gp120 linked by the linker to a second variable domain with binding affinity to HIV gp41.

The heavy chain of the antibody may be one of SEQ ID NO 3, SEQ ID NO 4, and SEQ ID NO 8. The light chain of the antibody may be one of SEQ ID NO 5, SEQ ID NO 6 and SEQ ID NO 7. The light chain is not SEQ ID NO 7 when the heavy chain is SEQ ID NO 8. The at least one variable domain with binding affinity to HIV gp120 may include domains 1 and 2 of CD4.

In an exemplary embodiment of the present invention, a method of treating an HIV infection is provided, including:

administering to a patient infected with HIV at least one of an antibody and a genetic construct capable of producing the antibody in the patient, said antibody having: at least one domain with binding affinity to HIV gp120; and at least one domain with binding affinity to HIV gp41. At least one of a heavy chain and a light chain of the antibody has a domain with binding affinity to HIV gp120 linked by a linker to a domain with binding affinity to HIV gp41. The antibody may have been incorporated into an immunoconjugate having at least one of a toxin and a cytotoxic agent.

In an exemplary embodiment of the present invention, a method of neutralizing HIV virus is provided, including: administering at least one of an antibody and a genetic construct capable of producing the antibody, said antibody having: at least one domain with binding affinity to HIV gp120; and at least one domain with binding affinity to HIV gp41. At least one of a heavy chain and a light chain of the antibody has a domain with binding affinity to HIV gp120 linked by a linker to a domain with binding affinity to HIV gp41. The least one of an antibody and a genetic construct capable of producing the antibody may be administered to a subject infected with HIV. The least one of an antibody and a genetic construct capable of producing the antibody may be administered to a subject at risk of exposure to HIV.

DETAILED DESCRIPTION

Figure 1:
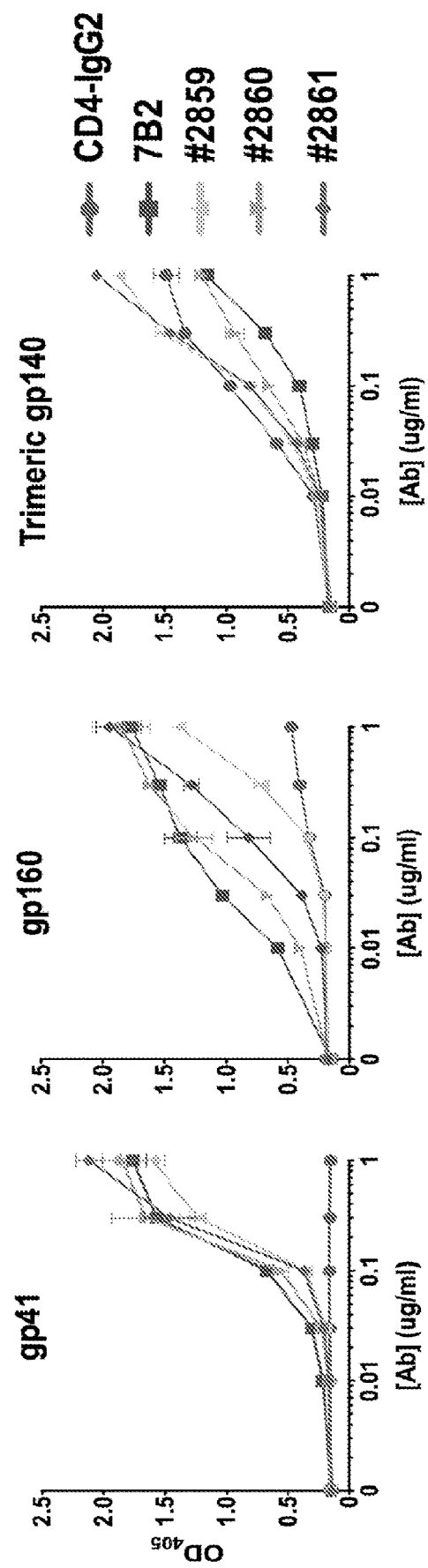
FIG. 1 is a set of three graphs showing binding qualities of constructs and parental antibodies to antigens, according to an exemplary embodiment of the present invention.

The present invention relates generally to bispecific antibodies, asymmetric antibodies, antibody-like molecules and methods of treating HIV infections. Before explaining at least one embodiment of the invention in detail, it is to be understood that the invention is not necessarily limited in its application to the details set forth in the following description or exemplified by any examples. The invention is capable of other embodiments or of being practiced or carried out in various ways.

Throughout this disclosure, the term "antibody" may indicate a classical antibody, but also an antibody-like molecule, a protein, a fragment thereof, or any combination of these. "Antibody" may include proteins, fragments, glycoproteins (e.g., CD4), or portions thereof attached or linked to antibodies and/or variable domains of antibodies. Sequences encoding CD4 (domains 1 and 2) are referred to as variable domains in this application. These terms are intended to be illustrative in nature, and certainly not limiting.

Any antibody or antibody fragment of the present invention, whether attached to other sequences or not, can also include insertions, deletions, substitutions, or other selected modification or particular regions or specific amino acids residues, provided the activity of the antibody or antibody fragment is not significantly altered or impaired compared to the non-modified antibody or antibody fragment. These modifications can provide for some additional property.

Embodiments of the present invention may be administered to a subject in a pharmaceutical composition, which may be any acceptable carrier. Effective dosages and schedules for administering embodiments of the present invention may be determined empirically. Embodiments may be administered to neutralize, treat, prevent or eradicate HIV infection. Embodiments of the present invention may be used in gene therapy techniques for HIV. In certain embodiments, genetic constructs capable of inducing production of antibodies of the present invention may be administered to a patient in need thereof.

Embodiments of the present invention provide an antibody having at least one variable domain with binding affinity to HIV gp120 and at least one variable domain with binding affinity to HIV gp41. At least one of a heavy chain and a light chain of the antibody may have a variable domain with binding affinity to HIV gp120 linked by a linker to a variable domain with binding affinity to HIV gp41.

Embodiments of the present invention include synthetic genes, which encode novel antibody constructs of the present invention. Embodiments of the present invention include monoclonal antibodies to HIV having at least one dual variable domain chain with the dual domains linked by the linker. Embodiments of the present invention may be derived from monoclonal antibody 7B2.

Embodiments of the present invention provide methods of HIV treatment and neutralization. HIV virus may be neutralized and/or eliminated with novel constructs of the present invention. Novel constructs of the present invention may be administered for neutralization of HIV loads and/or may include a cytotoxic agent to trigger cytotoxic activities in infected cells. Embodiments of the present invention provide therapeutic treatments for HIV infections using novel DVD-Ig constructs. Embodiments of the present invention provide methods of preventing HIV infection by administering novel antibody constructs. The novel constructs of the present invention may be administered as part of a pharmaceutical composition or as genetic constructs to be made into antibodies by the patient's own cells.

An embodiment of the present invention includes an antibody having a heavy chain of SEQ ID NO 3 and a light chain of SEQ ID NO 5—construct #2816. An embodiment of the present invention includes an antibody having a heavy chain of SEQ ID NO 4 and a light chain of SEQ ID NO 6—construct #2817. An embodiment of the present invention includes an antibody having a heavy chain of SEQ ID NO 8 and a light chain of SEQ ID NO 5—construct #2858. An embodiment of the present invention includes an antibody having a heavy chain of SEQ ID NO 3 and a light chain of SEQ ID NO 7—construct #2859. An embodiment of the present invention includes an antibody having a heavy chain of SEQ ID NO 8 and a light chain of SEQ ID NO 6—construct #2860. An embodiment of the present invention includes an antibody having a heavy chain of SEQ ID NO 4 and a light chain of SEQ ID NO 7—construct #2861.

It is understood that upon binding of gp120 to CD4, the HIV Env protein on the surface of the virion undergoes a conformational change that exposes several key epitopes on both gp120 and gp41 that are vulnerable to attack by our immune systems. Substantial work has been published on the potent neutralization activity of CD4 binding site (CD4bs) antibodies like VRC01 and b12. This class of antibodies binds to the CD4 binding site on gp120 to block interaction. In addition to blocking the ability of the virus to recognize its cognate receptors, the conformation changes expose areas of gp41 necessary for membrane fusion and cell entry.

It has been known that addition of soluble CD4 (sCD4) enhances immunoconjugate activity by changing the conformation of the Env protein. Recently more CD4-inducible (CD4i) antibodies have been characterized; however, effective neutralization requires the presence of CD4. This led to the problem of how to deliver both a soluble form of CD4 and the monoclonal antibody simultaneously, which was solved by fusing the relevant portion of CD4 to a CD4i-antibody through a variety of linkers. Several CD4i reagents, such as 17b, E51, and m9, have been fused to sCD4 for enhanced activity. A range of CD4-i reagents have been produced from large, bispecific antibodies constructs to smaller single-chain immunoadhesins. While the smaller scFv forms may result in higher tissue penetration and epitope access, they are naturally less avid and limited in their ability to stimulate the immune system through Fc interactions and antibody dependent cell cytotoxicity (ADCC). In the case of CD4-7B2 constructs, the CD4 subunits are not only advantageous for increasing neutralization but enhance exposure of the precise epitope 7B2 requires.

Contemporary fusion antibodies were included in studies alongside a panel of CD4-7B2 DVD-Igs embodiments of the present invention. This allowed for a comparison of the effects of CD4 fusion versus mixing CD4i-antibodies with CD4-IgG. It would be much more efficient to supply a single engineered form of CD4-7B2, especially if it neutralizes an extremely broad range of HIV isolates. In embodiments of the present invention, CD4-7B2 IgGs were engineered to function as both an immunoconjugate and a neutralizing antibody. Results show that fusion of CD4 to a single chain of 7B2 through a linker, such as a flexible linker or a helical linker, creates an optimal configuration for binding the Env subunits, neutralizing the infectivity of the virus, and killing cells already infected and producing the virus.

In addition to neutralization, immunoconjugates (IC) may be beneficial in reducing infectivity. HAART has contributed to a substantial decrease in viral loads, yet there is no vaccine or cure available. A potential approach would be use of an IC to eliminate the latent reservoir through an "activate and purge" strategy advocated by inducing reactivation of integrated viral genomes and subsequent killing of infected cells. An IC is a chimeric protein that combines the targeting specificity of an antibody with the cellular effects of a toxin. Correctly chosen parental antibodies can be incorporated into ICs which bind viral proteins on the surface of infected cells where they are subsequently phagocytized, intracellularly processed, and then activated to kill the infected cell. Certain toxic molecules can induce apoptosis over necrosis which helps reduce spread of virus to neighboring healthy cells. In this protocol, an HIV-activating agent would be administered first, and then treatment with ICs would deliver apoptosis-inducing drugs into infected cells. Early attempts have proved the concept that ICs can effectively kill infected cells in vitro using a CD4bs antibody and a bacterial exotoxin. In example embodiments of the present invention, ricin A chain (RAC) was utilized due to its cytotoxic attributes and relative stability over time. Extensive studies have shown how both native ricin and conjugated ricin are trafficked and activated to kill cells in vitro and in vivo. The new CD4-7B2 constructs of the present invention represent potential therapeutics with an increased breadth of neutralization and the unparalleled cell-targeted killing ability of ICs.

In an embodiment of the invention, the variable domains of the bispecific antibody disclosed herein comprise domains from antibodies that may bind the CD4 binding site, variable loops, and/or glycans of gp120, and the variable domains from the anti-gp41 monoclonal antibody 7B2, or other gp41 antibodies. The CD4-binding site of gp120 may be targeted with either CD4-itself (for example, soluble CD4) or an antibody or fragment thereof specific for this binding site. Such antibody or fragment thereof may be monoclonal in nature. In embodiments of the present invention, the variable domains may be linked by a linker (also known as an inter-V chain linker). Notably, unique construction of the inter-V chain linker may comprise synthetic peptides with either unordered or helical conformations.

Unlike conventional double-domain antibodies, which are symmetric assemblies of two identical heavy chains and two identical light chains, each containing identical variable regions, embodiments of the present invention may comprise asymmetric double variable domain antibodies, wherein the variable regions are not identical. For example, in one embodiment, a heavy chain may contain a $V_{H1}$-L-$V_{H2}$, and the light chain variable region may consist of $V_{L2}$ only. It should be noted that any combination thereof may be used to make the asymmetric double-variable domain antibodies, such as antibodies that may bind gp120 and gp41. In embodiments of the present invention, symmetric or asymmetric heavy and light chains may be used.

It is generally known that tetrameric, symmetrical CD4-IgG neutralizes better than other CD4-IgG constructs, suggesting that symmetrical CD4-anti-gp41 antibodies may be effective neutralization antibodies. However, the neutralization capabilities of the symmetrical CD4-anti-gp41 antibodies were poor when experimentally tested, suggesting that CD4-anti-gp41 antibodies or antibody-like molecules may be poor candidates for HIV-neutralization antibodies. Surprisingly, when asymmetric CD4-anti-gp41 antibodies were constructed and tested in TZM-bl cells against a panel of tier 1 and tier 2 clade B and C viruses, such antibodies had astonishingly high neutralization capacity. These surprising results suggest that the asymmetric structure of these antibodies may provide increased neutralization capacity.

An advantage of the disclosed invention is that the antibodies work well as neutralizing antibodies. This is a unique advantage to these antibodies, as other constructs were not as effective as neutralizing antibodies. For example, preliminary tests performed using 7B2-CD4 hybrid IgG molecules in TZM-bl cells against a panel of tier 1 and tier 2 clade B and C viruses demonstrate that these constructs may be highly effective neutralizing antibodies. The 7B2 antibody served as a reference antibody in these tests, and the CH01-31 antibody served as a positive control. In particular, the results from this experiment demonstrate that CD4-anti-gp41 hybrid proteins disclosed herein are potent neutralizers.

Embodiments of the invention may be employed to treat or prevent HIV. In one such embodiment, the antibodies may be used as immunoconjugates, conjugated to a second molecule. For example, the second molecule may be a toxin, a label, a radioisotope, a drug, or a chemical compound.

In other embodiments, the antibodies disclosed herein may be used as neutralizing antibodies, passively administered or given via gene therapies. Supporting these approaches, preliminary data suggests that certain constructs may be highly effective neutralizing antibodies.

Generally, embodiments of the present invention comprise double variable domain (DVD) antibodies that may bind in a tetravalent fashion to antigens of Env, such as gp120 and gp41. Antibodies to gp41 and/or gp120 of Env may provide important neutralization components necessary for an effective HIV/AIDS therapeutic, as Env is the only HIV protein displayed fully intact on the surface of HIV-infected cells. Embodiments of the present invention may incorporate monoclonal antibody 7B2, which binds to the external loop of gp41. In certain embodiments of the present invention, asymmetrical DVD antibodies are provided.

Embodiments of the present invention provide immunoglobulins (Igs) engineered to improve HIV neutralization and/or delivery of cytotoxic agent to infected cells. Example embodiments include CD4-Igs containing domains 1 and 2 of human CD4 attached to either heavy, light, or both chains of full-length human 7B2 antibody, an IgG1/κ anti-gp41 antibody. Embodiments may be engineered using helical linkers or other flexible sequences. For example, a helix-creating sequence (SEQ ID NO 9) or a combination of helical and flexible sequences (SEQ ID NO 10) may be incorporated as linkers. Embodiments may be created by expressing H and L chains in different plasmids and co-transfecting the H and L chains into 293F cells, creating CD4/7B2 chimeric Igs with various CD4-antibody conformations and linker usage. A description of example embodiments of the present invention is set forth in Table 1, where construct nos. 2816, 2817, and 2858 to 2861 represent novel embodiments of the present invention.

TABLE 1

Description of Parental Abs and Chimeric Constructs

| NAME | H Chain | L Chain | Linker | Specificity |
|---|---|---|---|---|
| 7B2 | 7B2 (γ1) | 7B2 (κ) | — | gp41 |
| CD4-IgG2 | CD4-IgG2 | CD4 (κ) | — | gp120 |
| CD4/7B2-Ig #2816 | CD4-2H2-7B2 | CD4-2H2-7B2 | 2H2* | gp41/gp120 |
| CD4/7B2-Ig #2817 | CD4-H4-7B2 | CD4-H4-7B2 | H4* | gp41/gp120 |
| CD4/7B2-Ig #2858 | 7B2 | CD4-2H2-7B2 | 2H2 | gp41/gp120 |
| CD4/7B2-Ig #2859 | CD4-2H2-7B2 | 7B2 | 2H2 | gp41/gp120 |
| CD4/7B2-Ig #2860 | 7B2 | CD4-H4-7B2 | H4 | gp41/gp120 |
| CD4/7B2-Ig #2861 | CD4-H4-7B2 | 7B2 | H4 | gp41/gp120 |

*2H2 is two flexible domains flanking a helical core [(GGGGS)$_{x2}$-(EAAAK)$_{x4}$-(GGGGS)$_{x2}$)] H4 is the helical core only: [A-(EAAAK)$_{x4}$-A]

Full-length DVD-IgsCD4/7B2 chimeras with appropriately linked subunits were produced in 293F cells in sufficient quantity and purity to test their ability to function as immunoconjugates, bind to infected cells, and neutralize HIV.

Binding of DVD-Igs to Recombinant and Native Antigen

ELISA was used to demonstrate binding of each construct to cognate antigens: gp41 peptide, recombinant gp160, or trimeric gp140. See, e.g., FIG. 1. ELISA plates were coated with respective antigens, incubated with serial dilutions of Abs, and probed with an AP-conjugated anti-human IgG secondary antibody. FIG. 1 has three graphs showing the binding qualities of each construct and parental antibodies to gp41, gp160 and trimeric gp140. All CD4-Ig constructs bound each antigen in the nanomolar range. As expected, CD4-IgG2 does not have any reactivity with gp41, and binds the more "native" trimer gp140 better than non-native gp160. 7B2, which identifies a linear epitope, binds well to the peptide and gp160, but less well to trimeric gp140, suggesting this epitope may be partially occluded in the trimer. There was no preference for antigen binding to gp41 based on attachment of CD4 to the light (#2860) or heavy chain (#2859, 2861), suggesting CD4 does not hinder accessibility of 7B2 to its epitope. Studies with trimeric gp140 showed that CD4/7B2 chimeras with CD4 on the heavy chain only (#2859, 2861) exhibited stronger binding than parental 7B2. And at the highest Ig concentration, #2861 exhibited the strongest binding to all antigens tested. Overall, the DVD-Igs perform as well or better than 7B2 and sCD4-IgG2, especially in the assays using the trimeric form of gp140, suggesting that recognition of the a more native conformation improves cumulative binding.

Figure 2:
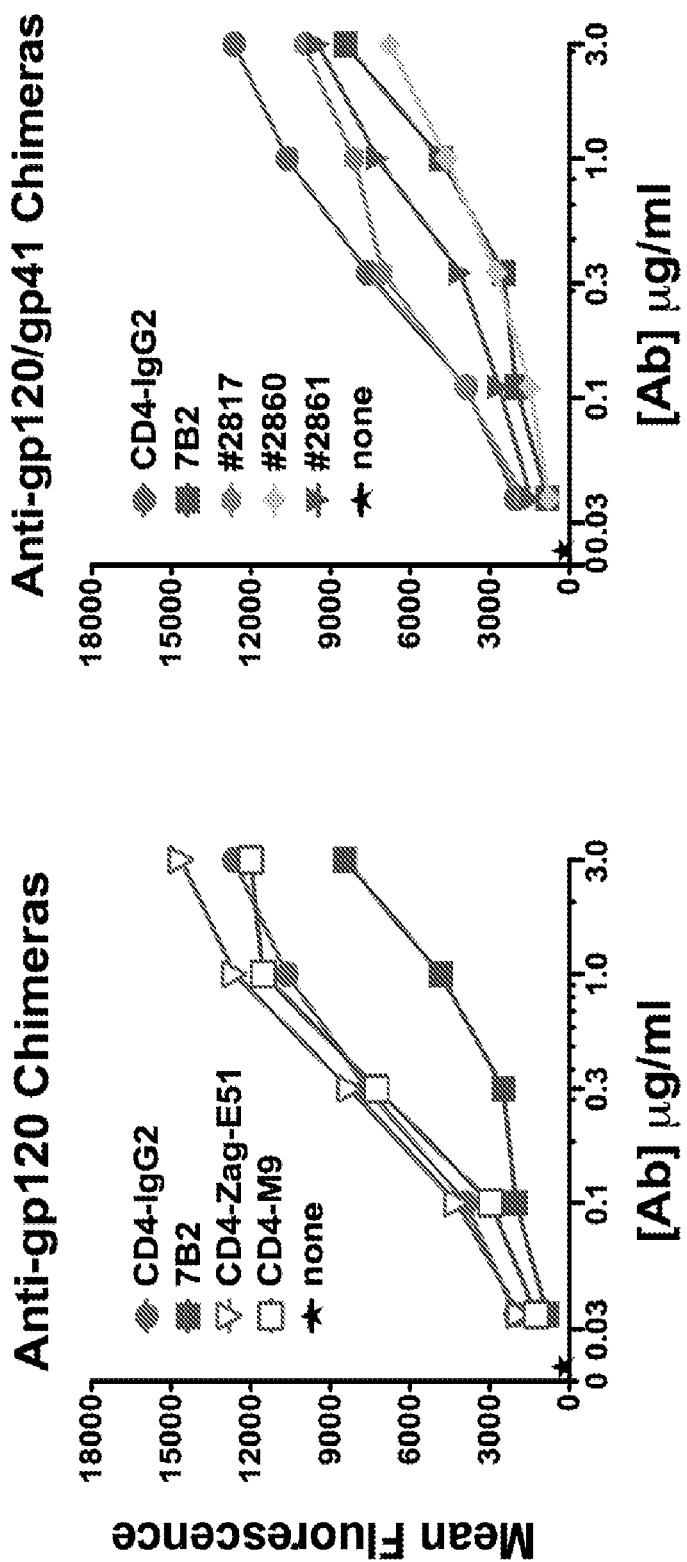
FIG. 2 is a set of two graphs showing indirect immunofluorescence and flow cytometry analysis of binding qualities to persistently infected H9/NL4-3 cells, according to an exemplary embodiment of the present invention.

To test recognition of native Env by the chimeras, indirect immunofluorescence and flow cytometry were used to analyze binding to persistently infected H9/NL4-3 cells. See, e.g., FIG. 2. In addition to the novel constructs, which target both gp41 and gp120, binding of a set of gp120-specific CD4-Ig chimeras designed by others were also examined. It was found that binding of the CD4/Ig chimeras specific solely for gp120 exceeded binding of the constructs specific for both gp120 and gp41. Of the gp120/gp41 specific chimeras, construct #2817, with CD4 fused to both heavy and light chains, bound best.

Immunoconjugate Cytoxicity

Figure 3:
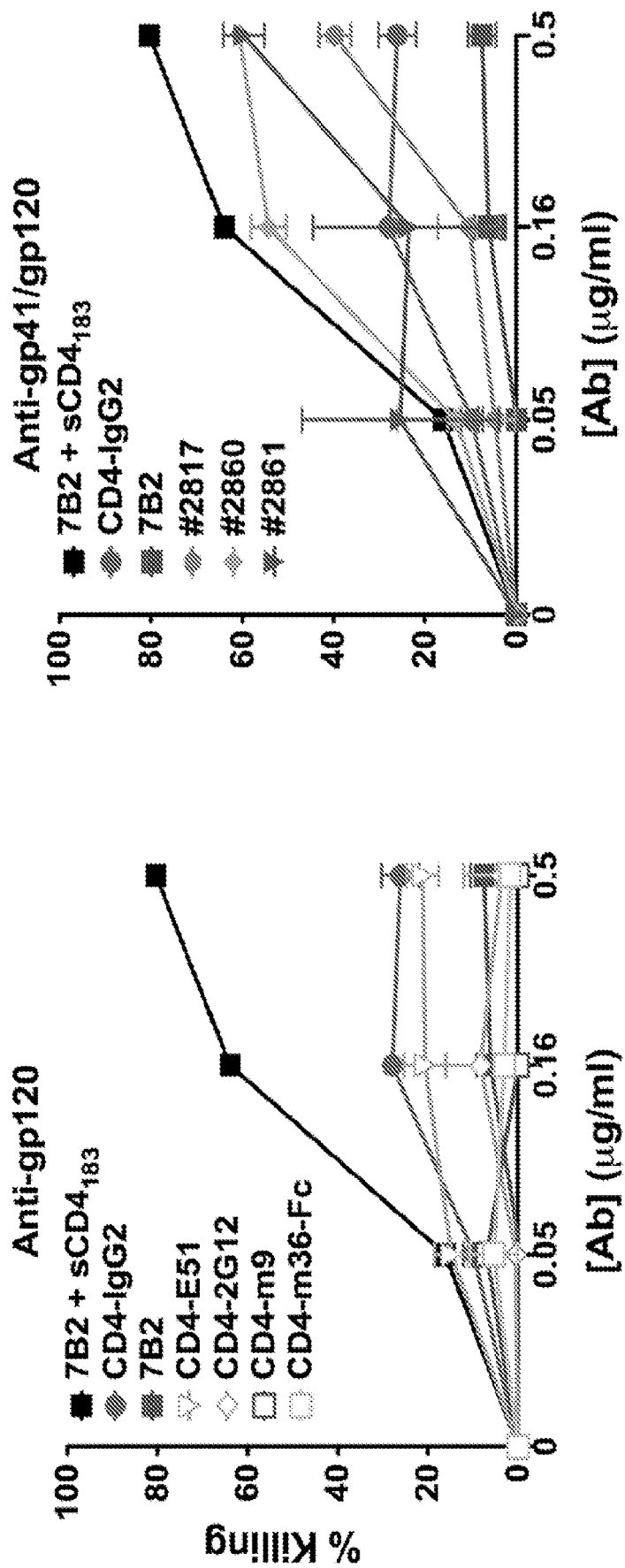
FIG. 3 is a set of two graphs showing indirect immonoconjugate assays of anti-gp120 and anti-gp41/gp120 constructs, according to an exemplary embodiment of the present invention.

To determine whether the novel chimeras with CD4 linked to an anti-Env antibody can function as immunoconjugates to deliver cytotoxic agents to HIV-infected cells as a means to eradicate HIV infection, indirect immunoconjugate assay was used to compare the constructs. H9/NL4-3 cells were incubated with serial dilutions of Ab, then a ricin A chain conjugated to anti-IgG secondary Ab was added. Cell viability was measured after 3 days. 7B2 was highly effective in targeting the toxin when sCD4 was present, but ineffective in its absence. See, e.g., FIG. 3. CD4-Igs exhibited enhanced cytotoxicity compared to either parental antibody alone and to all other CD4-linked constructs. Bispecific CD4/7B2 targeting gp41 and gp120 exhibited more potent cytotoxicity than similar constructs only targeting gp120. No chimera was more effective than 7B2+sCD4. Among the CD4/7B2 constructs, those with two CD4 per construct (#2860 and #2861) outperformed the construct tetravalent with CD4 (#2817). The chimeras to the target cells and immunoconjugate killing did not correlate each other. Those binding to gp120 alone attached to the target cell better than those binding gp120/gp41, but killed the same cells less well. Similarly the CD4/7B2 construct tetravalent for CD4 attached best, but was least affective for delivering toxins.

HIV Neutralization

Figure 4:
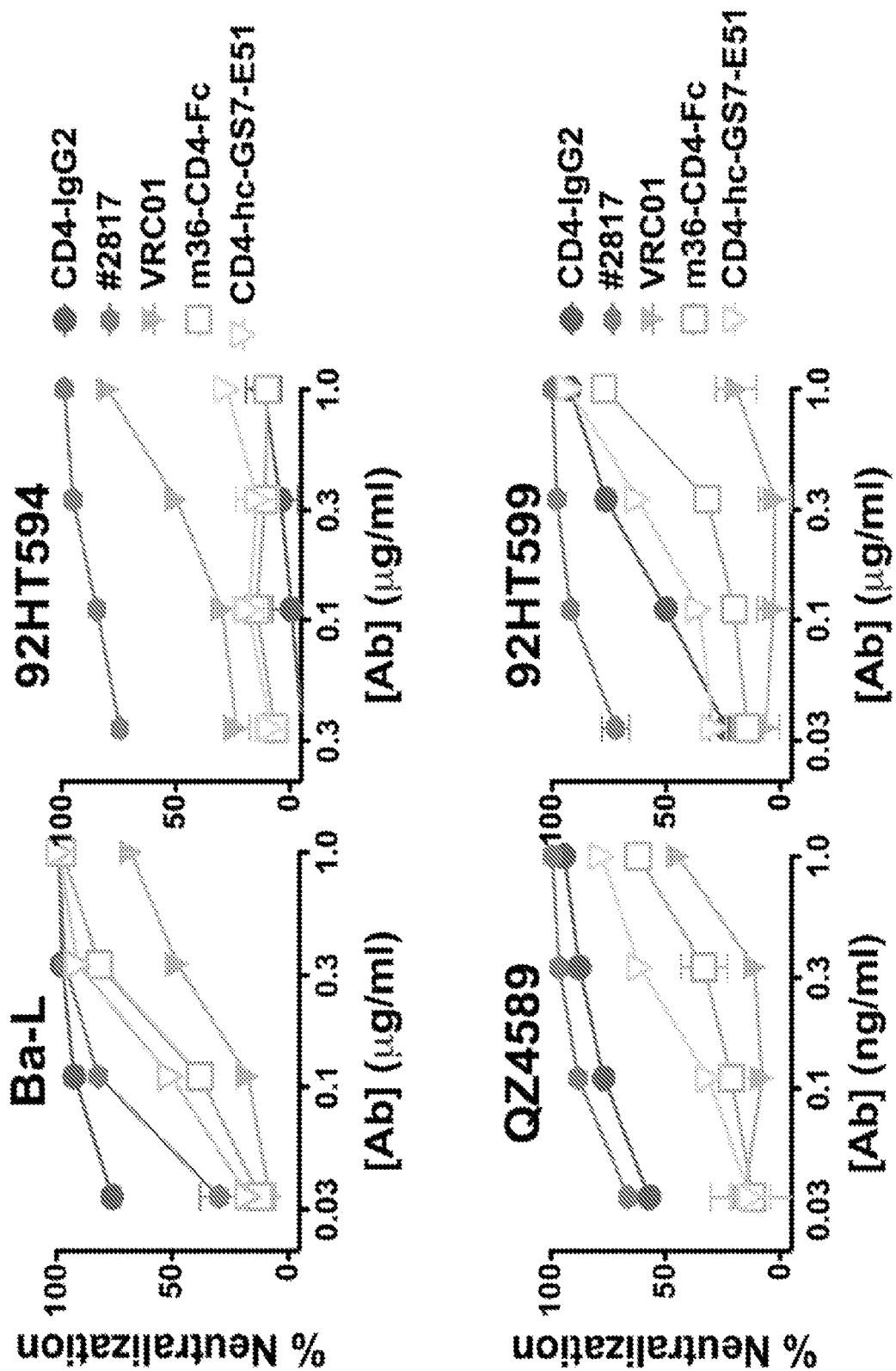
FIG. 4 is a set of four graphs showing assay results for neutralization of viral isolates, according to an exemplary embodiment of the present invention.
Figure 5:
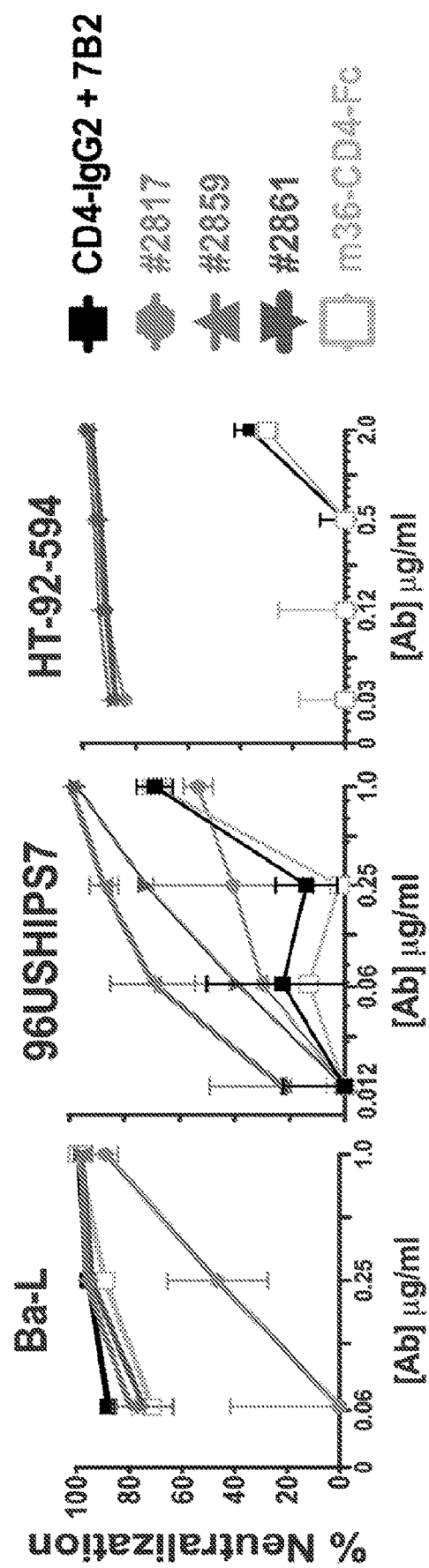
FIG. 5 is a set of three graphs showing assay results for neutralization of viral isolates, according to an exemplary embodiment of the present invention.

Although 7B2 has been shown to be an effective immunoconjugate, it cannot effectively neutralize most strains of HIV in conventional assays of neutralization. On the other hand, CD4-IgG2 contains both the gp120 binding site and the immunoglobulin constant region, and makes an effective neutralizing antibody. To test the neutralization ability of CD4/7B2-Ig constructs, both CXCR4 and CCR5-tropic HIV isolates were used with a TZM-bl luciferase assay. Infectious virus stocks were premixed with dilutions of antibodies, incubated with TZM-b1 cells for 3 days and then luciferase activity was assayed. Constructs with CD4 linked to both chains (#2817), the parental CD4-IgG2, and a panel of other CD4-linked immunoadhesins to four different HIV virus strains were tested first. In all isolates tested, #2817 exhibited excellent neutralization activity and outperformed all other constructs. See, e.g., FIG. 4. In FACS experiments with HIV-infected cells, anti-gp120 constructs showed strong binding. Here they are able to neutralize several isolates at the highest concentrations but quickly lose efficacy. VRC01 is the most effective for Ba-L and HT-594, while CD4/E51 neutralizes QZ4589 and HT-599. However, #2817 consistently displays enhanced neutralization of all four strains across all concentrations. Other configurations of CD4/7B2-Igs were tested against viral isolates ranging in difficulty to neutralize from easy (Ba-L) to hard (HT-92-594). FIG. 5 shows that constructs carrying CD4 on the heavy chain only (#2859 and 2861) neutralized all strains tested more efficiently than #2817 or any other chimeras in the panel, even better than parental CD4-IgG2, which has been used in phase II clinical trials. The most striking results were observed in the most difficult to neutralize strain, HT-92-594. The CD4/7B2-Igs #2859 and #2861 neutralized at >1000× lower concentration than any other CD4 chimeric construct.

Further tests of neutralization were performed at the Duke University HIV neutralization reference laboratories. Parental antibodies (7B2, CD4-IgG2), subunits (sCD4), and CD4/7B2-Igs (#2859, 2860, 2861), were compared to a standard monoclonal antibody mixture (CH01-31). Neutralization of pseudovirus was tested in both TZM-b1 and A3R5.7 cells using tier 1 and 2 viruses from clades B or C. The CD4/7B2-Igs, especially #2861, showed broad and potent neutralizing activity across clades, consistently outperforming the parental antibodies, sCD4, or the Ch01-31 standard. Constructs with CD4 fused to the heavy chain (#2859 and 2861) outperformed the light chain fusion (#2860).

Materials and Methods

Reagents and Cells

H9 cells, human CD4+lymphoma cell line, were obtained from Dr. M Reitz (Institute of Human Virology, Baltimore, Md.). H9/NL4-3 cells are persistently infected with the NL4-3 molecular clone of HIV and retain a productive infection in virtually 100% of tissue culture cells. TZM-b1 cells (NIH AIDS Reagent Program, NIH-ARP) are HeLa cells expressing CD4, CCR5, and CXCR4, with a HIV-tat inducible luciferase and beta-galactosidase reporter genes. H9/NL4-3 and TZM-b1 cells were maintained at 37° in 5% $CO_2$ in RPMI 1640 medium with 10% fetal bovine serum (Gibco Invitrogen, Grand Island, N.Y.) as described elsewhere.

HIV isolates used in these studies were all Clade B, and include: NL4-3 (X4-tropic), Ba-L (R5-tropic), 92HT594 (X4/R5), 92HT599(X4), QZ4589 (R5), and 96USHIPS7 (R5). All isolates were obtained from NIH-ARP and grown in PHA blasts, with the exception of NL4-3, which was produced by the H9/NL4-3 cell line.

Soluble, two-domain CD4 (sCD4; NIH-ARP) and CD4-IgG2 (PRO542; Progenies Pharmaceuticals, Tarrytown, N.Y.) were used to observe CD4-mediated effects. Goat anti-human IgG (heavy+light chains) antibody was conjugated to fluorescein isothiocyanate (FITC; Invitrogen) for flow cytometric analysis. Deglycosylated ricin A chain (RAC; obtained from Ellen Vitetta) was conjugated to purified anti-human IgG for cytotoxicity assays.

Design and Production of Antibodies

Synthetic genes encoding CD4/7B2-Ig constructs shown in table 1 were synthesized, codon optimized for mammalian expression by GenScript (Piscataway, N.J.). Two additional mutations (T250Q and M428L) were introduced into the constant region of the heavy chain to increase in vivo half-life of the antibody. DNA sequences were cloned into the eukaryotic expression plasmid pcDNA3.1 (Invitrogen) using either restriction enzyme sites XbaII and PmeI for the heavy chain, or HindIII and EcoRI for the light chain.

All antibodies were produced by transient transfection in suspension 293F cells (Invitrogen, Carlsbad, Calif.) in serum-free Freestyle expression media, shaking at 120 rpm in 8% $Co_2$ at 37' for transient transfection. Synthetic Igs were purified by affinity chromatography on Protein A agarose beads (Invitrogen), and concentrated by Microcon YM-30k centrifugal filter (Millipore, Billerica, Mass.). All antibody concentrations were measured by bicinchoninic acid protein assay (Pierce, Rockford, Ill.) and confirmed using OD280. Microcapillary electrophoresis (Agilent Bioanalyzer, GE Healthcare) was used to determine molecular weights and purity of products, and confirm concentrations Domains 1 and 2 of CD4 were joined to 7B2 using two effective linkers from previous studies: SEQ ID NO: 9 or SEQ ID NO: 10. The variable domains of CD4 were fused to the N-terminus of either the 7B2 IgG1 heavy chain, 7B2 kappa light chain, or both, creating a set of full length CD4/7B2-Ig.

ELISA

The antibodies tested, including the novel constructs, were characterized based on binding to Env (gp160) or its subunits (gp41, 140) by indirect ELISA. The gp41 peptide has a linear sequence SEQ ID NO: 3 representing the epitope of 7B2. Gp160 antigen is a recombinant protein consisting of the gp120 portion of MN and the gp41 portion of LAI, designated MN/LAI (Quality Biological, Gaithersburg, Md.) and expressed in mammalian cells. Gp140 is a trimeric version derived from SF162 that was used to test binding to multimers. Immulon 2HB plates (Thermo, Walktham, Mass.) were coated with 1.0 ug/ml of antigen and the assay performed as described elsewhere, using AP-conjugated goat anti-human IgG (H+L chain specific) secondary antibody. ELISA plates were read at 405 nm at room temperature in a BioTek EL320 microplate reader (BioTek, Winooski, Vt.) at 5-15 minute intervals. Time points shown in figures have been chosen so that maximal binding was within the dynamic range of the reader. Data are presented as the mean and SEM of triplicate assays.

Indirect Immunofluorescence and Flow Cytometry

H9/NL4-3 cells (1×10^5) were stained for flow cytometry in 100 ul in round bottom 96 well plates (Costar, Lowell, Mass.). Serial dilutions of Ig in PBA were added to the cells in the presence or absence of 500 ng/ml sCD4. Cells were incubated 1 hr at room temperature, washed, then stained with FITC-conjugated goat anti-human IgG (H+L chain specific) secondary antibody for 1-4 hrs, washed twice and fixed in 100 ul of 2% paraformaldehyde. After a minimum of 4 hrs, 150 ul PBS was added. Cells were analyzed on a Becton-Dickinson LSR II (BD<Franklin Lakes, N.J.) with HTS plate reader. 10000 events were collected and data analyzed by Flo-Jo software (Treestar, Ashland, Oreg.). Forward scatter (FSC) and side scatter (SSC) gated data are represented as graphs of mean fluorescence. None of the parental or synthetic-Igs bound to uninfected H9 cells.

Cytotoxicity Assay

An indirect cytotoxicity assay was performed to screen unconjugated antibodies for their ability to kill infected cells. H9/NL4-3 cells (8×10^3) were plated in triplicate. Controls included: no cells (background) and cells in the absence of antibody/IC (uninhibited). Serial dilutions of antibodies were incubated with cells for 1 hr in the presence or absence of 300 µg/ml sCD4 in RPMI at 37°. The secondary IC was affinity purified goat anti-human IgG (Invitrogen) conjugated to deglycosylated ricin A chain by the long chain heterobifunctional cross linking reagent, succinimidyl 6-[3(2-pyridyldithio)proprionamido]hexanoate (Pierce), using protocols described elsewhere [ ]. The secondary IC was added to a final concentration of 500 ng/ml. The plates were then incubated for 3 days. For the final 6 hrs of incubation, MTS/PMS substrate (Promega, Madison, Wis.) was added to each well and plates read hourly at 490 nm. Results represent the mean and SEM of triplicate samples, and are plotted as "Percent Killing" using the formula % kill=100*[(no Ab-Ab)/No Ab] with the no cell background subtracted. Under these conditions, there was no cytotoxicity on uninfected H9 cells. To determine whether the IC activity of the DVD-Ig represented an improvement over that of the parental antibodies, a one-tailed t-test comparing the DVD-Ig to the most effective parental antibody at each concentration was performed.

Direct cytotoxicity assay was performed with antibodies conjugated to ricin A chain by the long chain heterobifunctional cross linking reagent, succinimidyl 6-[3(2-pyridyldithio)proprionamido]hexanoate (Pierce. H9/NL4-3 cells (8×10^3) were plated in triplicate in cRPMI in 96 well flat-bottom tissue culture plates (Costar). Control included: no cells (background) and cells in the absence of IC, and cells +/−500 µg/ml CD4-IgG2. Serial dilutions of ICs were incubated with cells for 3 days in RPMI at 37°. For the final 6 hrs of incubation, MTS/PMS substrate (Promega) was added to each well and plates read hourly at 490 nm. Results plotted similarly to indirect IC assay explained above.

Neutralization Assay

Neutralization of infectious HIV was measured in TZM-bl cells, using a luciferase-read out assay. Each antibody was assayed in triplicate. Experiments included: background controls (cells, no virus, no antibody) and infected cells in the presence or absence of antibody. TZM-bl cells (4×10^4 cells/ml) were plated in 96-well plates with black sides and clear, flat bottom wells (Costar) and incubated overnight at 37° to allow attachment. The following day, 50 ul of serially diluted antibodies in RPMI were mixed with 50 ul of a pretitered concentration of virus and incubated for 1 hr at room temperature, then added to the cells in the presence of diethylaminoethyl dextran (Sigma) 15 µg/ml, and incubated for 6 hrs at 37°. Medium was added to a total volume of 200 ul/well and plates incubated for 48 hr at 37°. For luciferase assays, medium was aspirated and 50 ul of Bright-Glo Lysis buffer (Promega) was added. Samples were frozen and thawed once, and incubated for 6 hr at room temperature with orbital shaking at 120 rpm. Then 10 ul of Bright-Glo luciferase substrate (Promega) was added and luminescence read on Bio-Tek KC4 plate reader as relative luminescence units. Results are displayed as percent neutralization (virus/no Ab=0%; no virus=100% neutralization) according to the formula: [1−(RLUAb−RLUbkgrd)/(RLUnoAb−RLUbackground)]*100.

Neutralization of pseudo-typed reference strains in TZM-bl and A3R5.7 cells was performed at the Duke University HIV neutralization reference laboratories, using established assays.

Antibody-Dependent Cellular Viral Inhibition (ADCVI)

Figure 6:
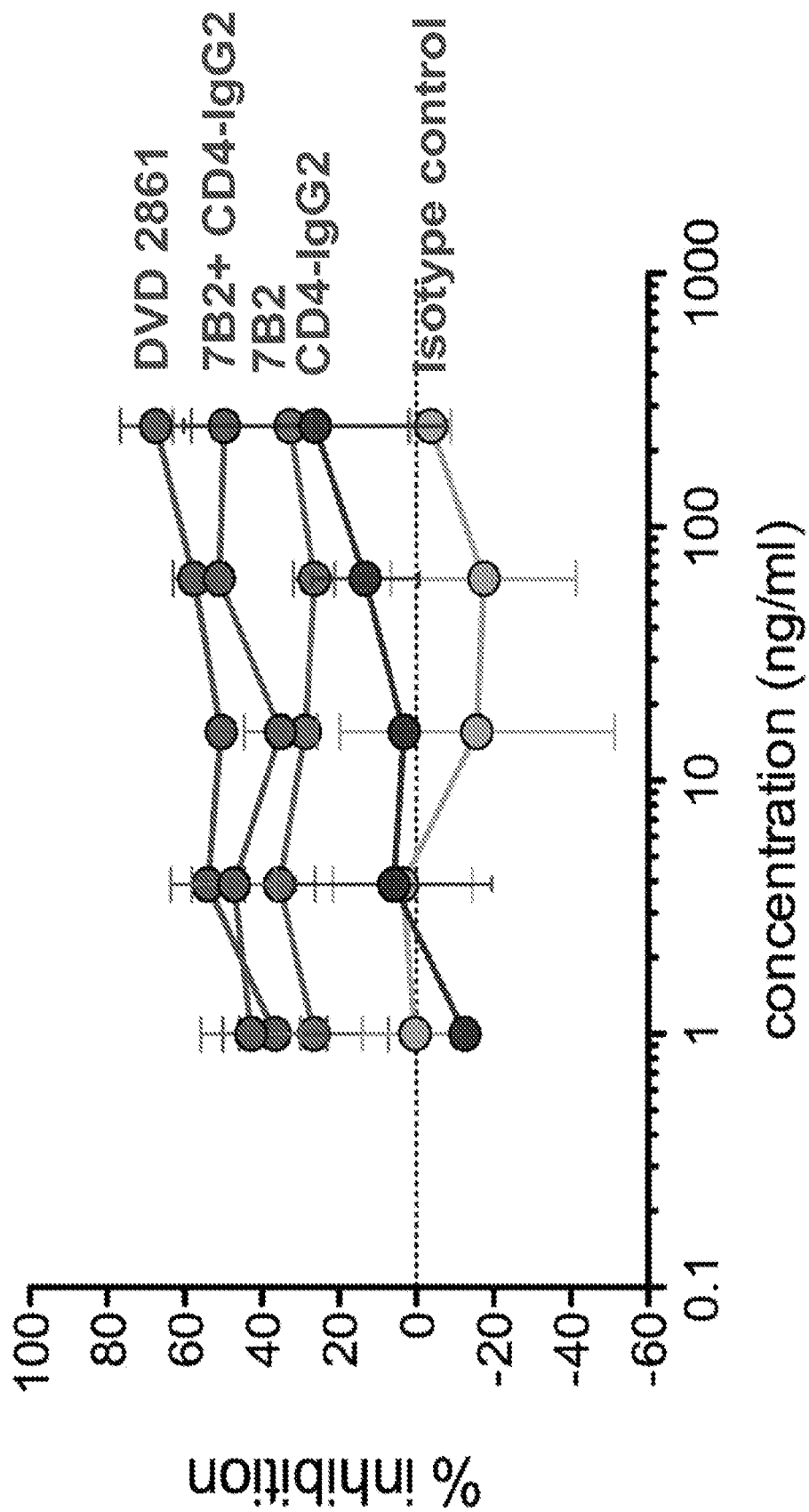
FIG. 6 is a graph showing assay results for antibody-dependent cellular viral inhibition, according to an exemplary embodiment of the present invention.

Embodiments of the present invention were tested to determine their ability to mediate ADCVI using human peripheral blood mononuclear cells (PBMC) as effector cells and CCR5+ CEM-NKr cells (AIDS Research and Reference Reagent Program) infected 2 days earlier with HIVBAL at an moi of 0.02 as target cells. See, e.g., FIG. 6. Briefly, target cells were washed twice in medium, then placed in wells of a V bottom plate at 104 cells per well. Target cells were incubated in triplicate with medium alone or diluted antibodies for 1 h at 37° C. and 5% $CO_2$. Freshly isolated PBMC (105 per well) were then added. Four days later, the cultures were split 1/4. On day 7, the medium in the wells was harvested, lysed with TritonX-100 detergent and analyzed for p24 content by ELISA. The % inhibition of infection was calculated after dividing the p24 concentration in antibody cultures by the average p24 concentration in control cultures containing effector and target cells alone. Construct no. 2861 showed greater efficacy than either of the parental antibodies, or a mixture of both. See, e.g., FIG. 6.

Antibody-Dependent Phagocytosis (ADP)

Figure 7:
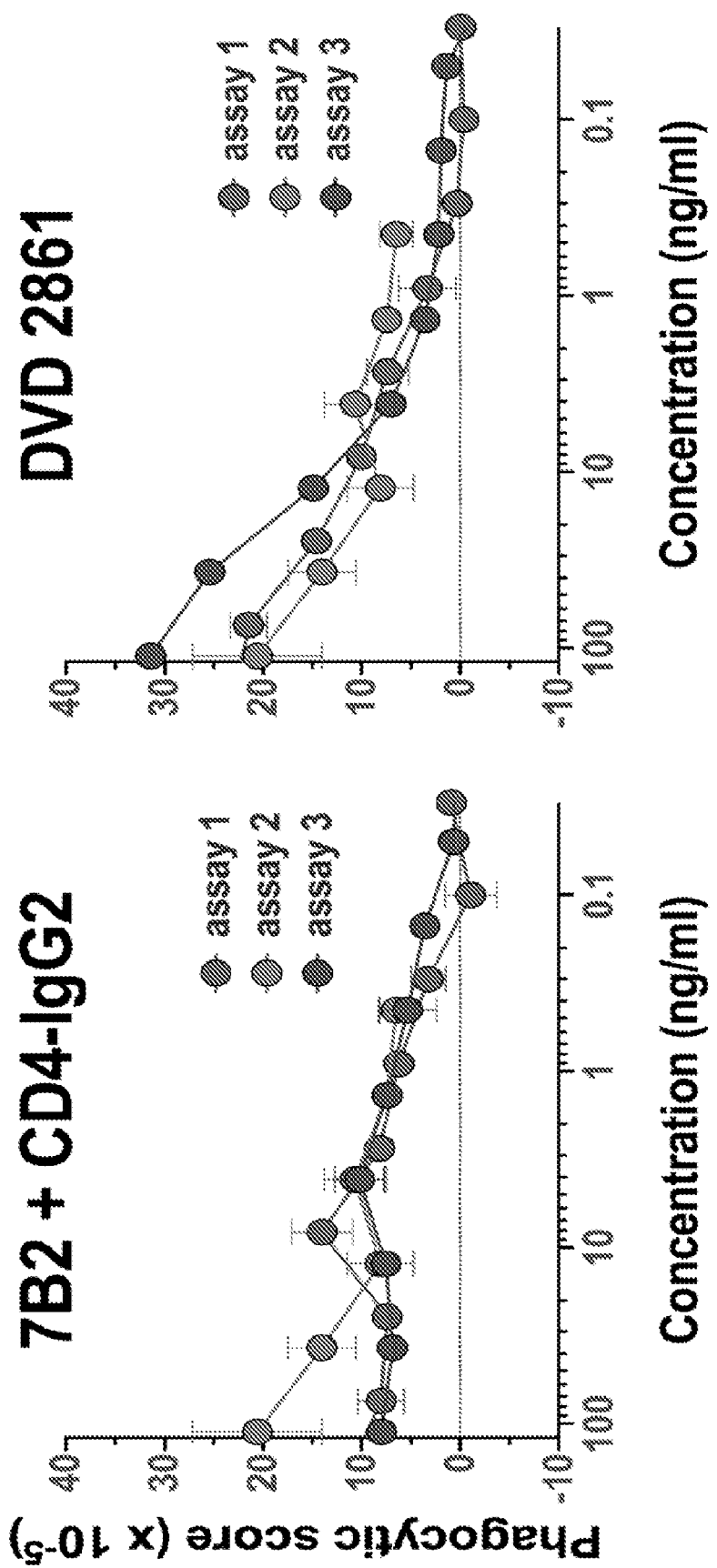
FIG. 7 is a graph showing assay results for antibody-dependent phagocytosis, according to an exemplary embodiment of the present invention.

Assays were performed using the THP-1 monocyte cell line and HIV gp140-coated fluorescent beads to evaluate ADP, specifically for construct no. 2861. See, e.g., FIG. 7. Briefly, 1.8×106 neutravidin-coated 1 µm Fluorospheres (Invitrogen) were treated with rabbit anti-His tag antibody (Pierce), then washed and reacted with recombinant gp140 SF162 protein (Immune Technology). After washing unbound material off the beads, they were incubated at 37° C. for 1 h with dilutions of antibody in triplicate wells of a V-bottom plate. THP-1 cells (2×104 per well) were then added and incubated at 37° C. in 5% CO2. After 4 h, the cells were washed with Ca+2/Mg+2-free DPBS and incubated at 37° C. for 10 min with 50 ul of 0.05% Trypsin/EDTA (Life Technologies). Cells were washed 2× in DPBS, re-suspended in 1% paraformaldehyde, then examined by flow cytometry for fluorescence. The phagocytic score was calculated by multiplying the number of bead-positive cells by the median fluorescent intensity. The average score obtained for triplicate wells of THP-1 and gp140-coated beads incubated in medium alone was subtracted from all other scores prior to calculating the average score for test samples. The ability of construct no. 2861 to promote phagocytosis of HIV-Env is greater than that of the combination of the two parental Abs. See, e.g., FIG. 7.

While the embodiments are described with reference to various implementations and exploitations, it will be understood that these embodiments are illustrative and that the scope of the invention is not limited to them. Many variations, modifications, additions, and improvements are also possible. Support for the present invention may be found in the attached documents and figures, all of which are expressly incorporated herein in their entirety by reference hereto.

Sequence Listing

```
SEQ ID NO 1
Length: 345
Type: amino acid
Organism: Human Immunodeficiency Virus
Other Information: gp 41 of Env
          10         20         30         40         50         60         70
           |          |          |          |          |          |          |
AVGIGALFLG FLGAAGSTMG AASMTLTVQA RQLLSGIVQQ QNNLLRAIEA QQHLLQLTVW GIKQLQARIL 80         90        100        110        120        130        140
           |          |          |          |          |          |          |
AVERYLKDQQ LLGIWGCSGK LICTTAVPWN ASWSNKSLEQ IWNHTTWMEW DREINNYTSL IHSLIEESQN 150        160        170        180        190        200        210
           |          |          |          |          |          |          |
QQEKNEQELL ELDKWASLWN WFNITNWLWY IKLFIMIVGG LVGLRIVFAV LSIVNRVRQG YSPLSFQTHL 220        230        240        250        260        270        280
           |          |          |          |          |          |          |
PTPRGPDRPE GIEEEGGERD RDRSIRLVNG SLALIWDDLR SLCLFSYHRL RDLLLIVTRI VELLGRRGWE 290        300        310        320        330        340
           |          |          |          |          |          |
ALKYWWNLLQ YWSQELKNSA VSLLNATAIA VAEGTDRVIE VVQGACRAIR HIPRRIRQGL ERILL SEQ ID NO 2
Length: 481
Type: amino acid
Organism: Human Immunodeficiency Virus
Other Information: gp 120 of Env
          10         20         30         40         50         60         70
           |          |          |          |          |          |          |
TEKLWVTVYY GVPVWKEATT TLFCASDAKA YDTEVHNVWA THACVPTDPN PQEVVLVNVT ENFNMWKNDM 80         90        100        110        120        130        140
           |          |          |          |          |          |          |
VEQMHEDIIS LWDQSLKPCV KLTPLCVSLK CTDLKNDTNT NSSSGRMIME KGEIKNCSFN ISTSIRGKVQ 150        160        170        180        190        200        210
           |          |          |          |          |          |          |
KEYAFFYKLD IIPIDNDTTS YKLTSCNTSV ITQACPKVSF EPIPIHYCAP AGFAILKCNN KTFNGTGPCT 220        230        240        250        260        270        280
           |          |          |          |          |          |          |
NVSTVQCTHG IRPVVSTQLL LNGSLAEEEV VIRSVNFTDN AKTIIVQLNT SVEINCTRPN NNTRKRIRIQ 290        300        310        320        330        340        350
           |          |          |          |          |          |          |
RGPGRAFVTI GKIGNMRQAH CNISRAKWNN TLKQIASKLR EQFGNNKTII FKQSSGGDPE IVTHSFNCGG 360        370        380        390        400        410        420
           |          |          |          |          |          |          |
EFFYCNSTQL FNSTWFNSTW STEGSNNTEG SDTITLPCRI KQIINMWQKV GKAMYAPPIS GQIRCSSNIT 430        440        450        460        470        480
           |          |          |          |          |          |
GLLLTRDGGN SNNESEIFRP GGGDMRDNWR SELYKYKVVK IEPLGVAPTK AKRRVVQREK R SEQ ID NO 3
Length: 710
Type: amino acid
Other Information: CD4-[2-helix-2]-7B2 DVR Heavy Chain
          10         20         30         40         50         60         70
           |          |          |          |          |          |          |
MNRGVPFRHL LLVLQLALLP AATQGKKVVL GKKGDTVELT CTASQKKSIQ FHWKNSNQIK ILGNQGSFLT 80         90        100        110        120        130        140
           |          |          |          |          |          |          |
KGPSKLNDRA DSRRSLWDQG NFPLIIKNLK IEDSDTYICE VEDQKEEVQL LVFGLTANSD THLLQGQSLT 150        160        170        180        190        200        210
           |          |          |          |          |          |          |
LTLESPPGSS PSVQCRSPRG KNIQGGKTLS VSQLELQDSG TWTCTVLNQO KKVEFKIDIV VLAFQKASGG 220        230        240        250        260        270        280
           |          |          |          |          |          |          |
GGSGGGGSLE AEAAAKEAAA KEAAAKEAAA KALEGGGGSG GGGSQVQLVQ SGGGVFKPGG SLRLSCEASG 290        300        310        320        330        340        350
```

```
                                                 Sequence Listing

|           |           |           |           |           |           |
   FTFTEYYMTW  VRQAPGKGLE  WLAYISKNGE  YSKYSPSSNG  RFTISRDNAK  NSVFLQLDRL  SADDTAVYYC 360         370         380         390         400         410         420
           |           |           |           |           |           |           |
   ARADGLTYFS  ELLQYIFDLW  GQGARVTVSS  ASTKGPSVFP  LAPSSKSTSG  GTAALGCLVK  DYFPEPVTVS 430         440         450         460         470         480         490
           |           |           |           |           |           |           |
   WNSGALTSGV  HTFPAVLQSS  GLYSLSSVVT  VPSSSLGTQT  YICNVNHKPS  NTKVDKKVEP  KSCDKTHTCP 500         510         520         530         540         550         560
           |           |           |           |           |           |           |
   PCPAPELLGG  PSVFLFPPKP  KDTLMISRTP  EVTCVVVDVS  HEDPEVKFNW  YVDGVEVHNA  KTKPREEQYN 570         580         590         600         610         620         630
           |           |           |           |           |           |           |
   STYRVVSVLT  VLHQDWLNGK  EYKCKVSNKA  LPAPIEKTIS  KAKGQPREPQ  VYTLPPSRDE  LTKNQVSLTC 640         650         660         670         680         690         700
           |           |           |           |           |           |           |
   LVKGFYPSDI  AVEWESNGQP  ENNYKTTPPV  LDSDGSFFLY  SKLTVDKSRW  QQGNVFSCSV  MHEALHNHYT

710
           |
   QKSLSLSPGK

SEQ ID NO 4
   Length: 690
   Type: amino acid
   Other Information: CD4-[helix]x4-7B2 DVR Heavy Chain
           10          20          30          40          50          60          70
           |           |           |           |           |           |           |
   MNRGVPFRHL  LLVLQLALLP  AATQGKKVVL  GKKGDTVELT  CTASQKKSIQ  FHWKNSNQIK  ILGNQGSFLT 80          90         100         110         120         130         140
           |           |           |           |           |           |           |
   KGPSKLNDRA  DSRRSLWDQG  NFPLIIKNLK  IEDSDTYICE  VEDQKEEVQL  LVFGLTANSD  THLLQGQSLT 150         160         170         180         190         200         210
           |           |           |           |           |           |           |
   LTLESPPGSS  PSVQCRSPRG  KNIQGGKTLS  VSQLELQDSG  TWTCTVLQNQ  KKVEFKIDIV  VLAFQKASLE 220         230         240         250         260         270         280
           |           |           |           |           |           |           |
   AEAAAKEAAA  KEAAAKEAAA  KALEQVQLVQ  SGGGVFKPGG  SLRLSCEASG  FTFTEYYMTW  VRQAPGKGLE 290         300         310         320         330         340         350
           |           |           |           |           |           |           |
   WLAYISKNGE  YSKYSPSSNG  RFTISRDNAK  NSVFLQLDRL  SADDTAVYYC  ARADGLTYFS  ELLQYIFDLW 360         370         380         390         400         410         420
           |           |           |           |           |           |           |
   GQGARVTVSS  ASTKGPSVFP  LAPSSKSTSG  GTAALGCLVK  DYFPEPVTVS  WNSGALTSGV  HTFPAVLQSS 430         440         450         460         470         480         490
           |           |           |           |           |           |           |
   GLYSLSSVVT  VPSSSLGTQT  YICNVNHKPS  NTKVDKKVEP  KSCDKTHTCP  PCPAPELLGG  PSVFLFPPKP 500         510         520         530         540         550         560
           |           |           |           |           |           |           |
   KDTLMISRTP  EVTCVVVDVS  HEDPEVKFNW  YVDGVEVHNA  KTKPREEQYN  STYRVVSVLT  VLHQDWLNGK 570         580         590         600         610         620         630
           |           |           |           |           |           |           |
   EYKCKVSNKA  LPAPIEKTIS  KAKGQPREPQ  VYTLPPSRDE  LTKNQVSLTC  LVKGFYPSDI  AVEWESNGQP 640         650         660         670         680         690
           |           |           |           |           |           |
   ENNYKTTPPV  LDSDGSFFLY  SKLTVDKSRW  QQGNVFSCSV  MHEALHNHYT  QKSLSLSPGK SEQ ID NO 5
   Length: 502
   Type: amino acid
   Other Information: CD4-[2-helix-2]-7B2 DVR Light Chain
           10          20          30          40          50          60          70
           |           |           |           |           |           |           |
```

```
                                    Sequence Listing

MTSTLPFSPQ  VSTPRSKFKR  ISSEFAATMN  RGVPFRHLLL  VLQLALLPAA  TQGKKVVLGK  KGDTVELTCT 80          90         100         110         120         130         140
        |           |           |           |           |           |           |
ASQKKSIQFH  WKNSNQIKIL  GNQGSFLTKG  PSKLNDRADS  RRSLWDQGNF  PLIIKNLKIE  DSDTYICEVE 150         160         170         180         190         200         210
        |           |           |           |           |           |           |
DQKEEVQLLV  FGLTANSDTH  LLQGQSLTLT  LESPPGSSPS  VQCRSPRGKN  IQGGKTLSVS  QLELQDSGTW 220         230         240         250         260         270         280
        |           |           |           |           |           |           |
TCTVLQNQKK  VEFKIDIVVL  AFQKASGGGG  SGGGGSLEAE  AAAKEAAAKE  AAAKEAAAKA  LEGGGGSGGG 290         300         310         320         330         340         350
        |           |           |           |           |           |           |
GSDIVMTQSP  DSLAVSPGER  ATIHCKSSQT  LLYSSNNRHS  IAWYQQRPGQ  PPKLLLYWAS  MRLSGVPDRF 360         370         380         390         400         410         420
        |           |           |           |           |           |           |
SGSGSGTDFT  LTINNLQAED  VAIYYCHQYS  SHPPTFGHGT  RVELRRTVAA  PSVFIFPPSD  EQLKSGTASV 430         440         450         460         470         480         490
        |           |           |           |           |           |           |
VCLLNNFYPR  EAKVQWKVDN  ALQSGNSQES  VTEQDSKDST  YSLSSTLTLS  KADYEKHKVY  ACEVTHQGLS

500
        |
SPVTKSFNRG  EC

SEQ ID NO 6
Length: 482
Type: amino acid
Other Information: CD4-[helix]x4-7B2 DVR Light Chain
       10          20          30          40          50          60          70
        |           |           |           |           |           |           |
MTSTLPFSPQ  VSTPRSKFKR  ISSEFAATMN  RGVPFRHLLL  VLQLALLPAA  TQGKKVVLGK  KGDIVELICT 80          90         100         110         120         130         140
        |           |           |           |           |           |           |
ASQKKSIQFH  WKNSNQIKIL  GNQGSFLTKG  PSKLNDRADS  RRSLWDQGNF  PLIIKNLKIE  DSDTYICEVE 150         160         170         180         190         200         210
        |           |           |           |           |           |           |
DQKEEVQLLV  FGLTANSDTH  LLQGQSLTLT  LESPPGSSPS  VQCRSPRGKN  IQGGKTLSVS  QLELQDSGTW 220         230         240         250         260         270         280
        |           |           |           |           |           |           |
TCTVLQNQKK  VEFKIDIVVL  AFQKASLEAE  AAAKEAAAKE  AAAKEAAAKA  LEDIVMTQSP  DSLAVSPGER 290         300         310         320         330         340         350
        |           |           |           |           |           |           |
ATIHCKSSQT  LLYSSNNRHS  IAWYQQRPGQ  PPKLLLYWAS  MRLSGVPDRF  SGSGSGTDFT  LTINNLQAED 360         370         380         390         400         410         420
        |           |           |           |           |           |           |
VAIYYCHQYS  SHPPTFGHGT  RVELRRTVAA  PSVFIFPPSD  EQLKSGTASV  VCLLNNFYPR  EAKVQWKVDN 430         440         450         460         470         480
        |           |           |           |           |           |
ALQSGNSQES  VTEQDSKDST  YSLSSTLTLS  KADYEKHKVY  ACEVTHQGLS  SPVTKSFNRG  EC SEQ ID NO 7
Length: 240
Type: nucleic acid
Other Information: 7B2 Light Chain
       10          20          30          40          50          60          70
        |           |           |           |           |           |           |
METPAQLLFL  LLLWLPDTTG  DIVMTQSPDS  LAVSPGERAT  IHCKSSQTLL  YSSNNRHSIA  WYQQRPGQPP 80          90         100         110         120         130         140
        |           |           |           |           |           |           |
KLLLYWASMR  LSGVPDRFSG  SGSGTDFILT  INNLQAEDVA  IYYCHQYSSH  PPTFGHGTRV  ELRRTVAAPS 150         160         170         180         190         200         210
        |           |           |           |           |           |           |
VFIFPPSDEQ  LKSGTASVVC  LLNNFYPREA  KVQWKVDNAL  QSGNSQESVT  EQDSKDSTYS  LSSTLTLSKA
```

```
                    220         230         240
                     |           |           |
         DYEKHKVYAC EVTHQGLSSP VTKSFNRGEC

SEQIDNO 8
         Length: 475
         Type: amino acid
         Other Information: Parent 7B2 Heavy Chain
                 10         20         30         40         50         60         70
                  |          |          |          |          |          |          |
         MDWTWRVLFL VAAATGAHSQ VQLVQSGGGV FKPGGSLRLS CEASGFTFTE YYMTWVRQAP GKGLEWLAYI 80         90        100        110        120        130        140
                  |          |          |          |          |          |          |
         SKNGEYSKYS PSSNGRFTIS RDNAKNSVFL QLDRLSADDT AVYYCARADG LTYFSELLQY IFDLWGQGAR 150        160        170        180        190        200        210
                  |          |          |          |          |          |          |
         VTVSSASTKG PSVFPLAPSS KSTSGGTAAL GCLVKDYFPE PVTVSWNSGA LTSGVHTFPA VLQSSGLYSL 220        230        240        250        260        270        280
                  |          |          |          |          |          |          |
         SSVVTVPSSS LGTQTYICNV NHKPSNTKVD KRVEPKSCDK THTCPPCPAP ELLGGPSVFL FPPKPKDTLM 290        300        310        320        330        340        350
                  |          |          |          |          |          |          |
         ISRTPEVTCV VVDVSHEDPE VKFNWYVDGV EVHNAKTKPR EEQYNSTYRV VSVLTVLHQD WLNGKEYKCK 360        370        380        390        400        410        420
                  |          |          |          |          |          |          |
         VSNKALPAPI EKTISKAKGQ PREPQVYTLP PSREEMTKNQ VSLTCLVKGF YPSDIAVEWE SNGQPENNYK 430        440        450        460        470
                  |          |          |          |          |
         TTPPVLDSDG SFFLYSKLTV DKSRWQQGNV FSCSVMHEAL HNHYTQKSLS LSPGK SEQ ID NO 9
         Length: 22
         Type: amino acid
         Other Information: helical linker
                 10         20
                  |          |
         LEAEAAAKEA AKEAAAKEA AAKALE SEQ ID NO 10
         Length: 46
         Type: amino acid
         Other Information: 2-Helix-2 linker
                 10         20         30         40
                  |          |          |          |
         GGGGSGGGGS LEAEAAAKEA AKEAAAKEA AAKALEGGGG SGGGGS
```

What is claimed is:

1. A pharmaceutical composition comprising an asymmetric double variable domain (DVD) antibody comprising at least one immunoglobulin heavy chain light chain cross-linked pair, wherein the immunoglobulin heavy chain-light chain pair comprises a first variable domain having binding affinity for an epitope of an HIV gp41 polypeptide and further comprising a second variable domain having binding affinity for an epitope of an HIV gp120 polypeptide, wherein the second variable domain is linked by a linker peptide to the first variable domain of the immunoglobulin heavy chain or immunoglobulin light chain, but is not linked to the first variable domains of both the immunoglobulin heavy chain and the immunoglobulin light chain.

2. The pharmaceutical composition of claim 1, wherein the second variable domain having binding affinity for an epitope of an HIV gp120 polypeptide is a CD4 polypeptide or a fragment thereof.

3. The pharmaceutical composition of claim 1, wherein the first peptide domain having binding affinity for an epitope of an HIV gp41 polypeptide is the immunoglobulin variable region of monoclonal antibody 7B2.

4. The pharmaceutical composition of claim 1, wherein, in a heavy chain-light chain pair, the heavy chain comprises a first variable domain linked to a second variable domain and the light chain comprises a first variable domain but not a second variable domain.

5. The pharmaceutical composition of claim 1, wherein in a heavy chain-light chain pair, the light chain comprises a first variable domain linked to a second variable domain and the heavy chain comprises a first variable domain but not a second variable domain.

6. The pharmaceutical composition of claim 1, wherein the linker peptide comprises a helical core.

7. The pharmaceutical composition of claim 1, wherein the linker peptide comprises a helical core having a flexible domain at both the N-terminus and the C-terminus thereof.

8. The pharmaceutical composition of claim 1, wherein the heavy chain has an amino acid sequence selected from the group consisting of: SEQ ID Nos.: 3, 4, and 8, and wherein the light chain has an amino acid sequence selected from the group consisting of: SEQ ID Nos.: 5, 6, and 7.

9. The pharmaceutical composition of claim 1, wherein the cross-linked heavy and light chains have cross-linked amino acid sequences selected from the group consisting of: SEQ ID Nos.: 3 and 5, 4 and 6, 8 and 5, 3 and 7, 8 and 6, and 4 and 7.

10. The pharmaceutical composition of claim 1, wherein the cross-linked heavy and light chains have amino acid sequences selected from the group consisting of: SEQ ID Nos.: 3 and 5, 4 and 6, 8 and 5, 3 and 7, 8 and 6, and 4 and 7.

11. The pharmaceutical composition of claim 1, wherein the linker peptide has an amino acid sequence according to SEQ ID NO: 9.

12. The pharmaceutical composition of claim 1, wherein the linker peptide has an amino acid sequence according to SEQ ID NO: 10.

13. The pharmaceutical composition of claim 1, wherein the artificial immunoglobulin is admixed with a pharmaceutically acceptable carrier.

14. The pharmaceutical composition of claim 1, wherein each of the heavy and the light chains is an expression product from an expression vector.

15. The pharmaceutical composition of claim 14, wherein at least one of the heavy and the light chain expression products from the expression vector has an N-terminal leader sequence attached thereto.

16. A method of reducing the infectivity of an HIV by contacting said virus with the pharmaceutical composition according to any of claims 1-15.

17. A method of reducing the viability of an HIV-infected cell by the steps of:
   contacting a cell infected with a strain of HIV with an asymmetric DVD-antibody of the pharmaceutical composition according to any of claims 1-15, whereby said DVD-antibody binds to a cell surface polypeptide of the infected cell forming a cell-DVD-antibody complex; and
   contacting said cell-DVD-antibody complex with a cytotoxic agent capable of specifically recognizing the cell-bound DVD-antibody, thereby delivering the cytotoxic agent to the HIV-infected cell and reducing the viability of an HIV-infected cell.

18. The method of claim 17, wherein the cytotoxic agent is an engineered anti-immunoglobulin IgG antibody conjugated to a cytotoxic polypeptide, wherein the engineered anti-immunoglobulin IgG antibody specifically binds to a constant region of the asymmetric DVD-antibody.

19. The method of claim 17, wherein the cytotoxic polypeptide is a ricin A chain.

* * * * *

SEQUENCE LISTING

<160> NUMBER OF SEQ ID NOS: 10

<210> SEQ ID NO 1
<211> LENGTH: 345
<212> TYPE: PRT
<213> ORGANISM: Human immunodeficiency virus
<220> FEATURE:
<221> NAME/KEY: MISC_FEATURE
<223> OTHER INFORMATION: Env gp41 of HIV

<400> SEQUENCE: 1

Ala Val Gly Ile Gly Ala Leu Phe Leu Gly Phe Leu Gly Ala Ala Gly
 1               5                  10                  15

Ser Thr Met Gly Ala Ala Ser Met Thr Leu Thr Val Gln Ala Arg Gln
             20                  25                  30

Leu Leu Ser Gly Ile Val Gln Gln Asn Asn Leu Arg Ala Ile
        35                  40                  45

Glu Ala Gln Gln His Leu Leu Gln Leu Thr Val Trp Gly Ile Lys Gln
 50                  55                  60

Leu Gln Ala Arg Ile Leu Ala Val Glu Arg Tyr Leu Lys Asp Gln Gln
 65                  70                  75                  80

Leu Leu Gly Ile Trp Gly Cys Ser Gly Lys Leu Ile Cys Thr Thr Ala
                 85                  90                  95

Val Pro Trp Asn Ala Ser Trp Ser Asn Lys Ser Leu Glu Gln Ile Trp
                100                 105                 110

Asn His Thr Thr Trp Met Glu Trp Asp Arg Glu Ile Asn Asn Tyr Thr
            115                 120                 125

Ser Leu Ile His Ser Leu Ile Glu Glu Ser Gln Asn Gln Gln Glu Lys
        130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                165                 170                 175

Ile Val Gly Gly Leu Val Gly Leu Arg Ile Val Phe Ala Val Leu Ser
                180                 185                 190

Ile Val Asn Arg Val Arg Gln Gly Tyr Ser Pro Leu Ser Phe Gln Thr
            195                 200                 205

His Leu Pro Thr Pro Arg Gly Pro Asp Arg Pro Glu Gly Ile Glu Glu
        210                 215                 220

Glu Gly Gly Glu Arg Asp Arg Asp Arg Ser Ile Arg Leu Val Asn Gly
225                 230                 235                 240

Ser Leu Ala Leu Ile Trp Asp Asp Leu Arg Ser Leu Cys Leu Phe Ser
                245                 250                 255

Tyr His Arg Leu Arg Asp Leu Leu Leu Ile Val Thr Arg Ile Val Glu
                260                 265                 270

Leu Leu Gly Arg Arg Gly Trp Glu Ala Leu Lys Tyr Trp Trp Asn Leu
            275                 280                 285

Leu Gln Tyr Trp Ser Gln Glu Leu Lys Asn Ser Ala Val Ser Leu Leu
 290                 295                 300

Asn Ala Thr Ala Ile Ala Val Ala Glu Gly Thr Asp Arg Val Ile Glu
305                 310                 315                 320

Val Val Gln Gly Ala Cys Arg Ala Ile Arg His Ile Pro Arg Arg Ile
                325                 330                 335

Arg Gln Gly Leu Glu Arg Ile Leu Leu
            340                 345

<210> SEQ ID NO 2
<211> LENGTH: 481
<212> TYPE: PRT
<213> ORGANISM: Human immunodeficiency virus
<220> FEATURE:
<221> NAME/KEY: MISC_FEATURE
<223> OTHER INFORMATION: Env gp120 of HIV

<400> SEQUENCE: 2

Thr Glu Lys Leu Trp Val Thr Val Tyr Tyr Gly Val Pro Val Trp Lys
 1               5                  10                  15

Glu Ala Thr Thr Thr Leu Phe Cys Ala Ser Asp Ala Lys Ala Tyr Asp
                 20                  25                  30

Thr Glu Val His Asn Val Trp Ala Thr His Ala Cys Val Pro Thr Asp
             35                  40                  45

```
Pro Asn Pro Gln Glu Val Val Leu Val Asn Val Thr Glu Asn Phe Asn
 50                  55                  60

Met Trp Lys Asn Asp Met Val Glu Gln Met His Glu Asp Ile Ile Ser
 65                  70                  75                  80

Leu Trp Asp Gln Ser Leu Lys Pro Cys Val Lys Leu Thr Pro Leu Cys
                 85                  90                  95

Val Ser Leu Lys Cys Thr Asp Leu Lys Asn Asp Thr Asn Thr Asn Ser
                100                 105                 110

Ser Ser Gly Arg Met Ile Met Glu Lys Gly Glu Ile Lys Asn Cys Ser
            115                 120                 125

Phe Asn Ile Ser Thr Ser Ile Arg Gly Lys Val Gln Lys Glu Tyr Ala
130                 135                 140

Phe Phe Tyr Lys Leu Asp Ile Ile Pro Ile Asp Asn Asp Thr Thr Ser
145                 150                 155                 160

Tyr Lys Leu Thr Ser Cys Asn Thr Ser Val Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Asn Asn Lys Thr Phe Asn Gly Thr Gly Pro
            195                 200                 205

Cys Thr Asn Val Ser Thr Val Gln Cys Thr His Gly Ile Arg Pro Val
210                 215                 220

Val Ser Thr Gln Leu Leu Leu Asn Gly Ser Leu Ala Glu Glu Glu Val
225                 230                 235                 240

Val Ile Arg Ser Val Asn Phe Thr Asp Asn Ala Lys Thr Ile Ile Val
                245                 250                 255

Gln Leu Asn Thr Ser Val Glu Ile Asn Cys Thr Arg Pro Asn Asn Asn
                260                 265                 270

Thr Arg Lys Arg Ile Arg Ile Gln Arg Gly Pro Gly Arg Ala Phe Val
            275                 280                 285

Thr Ile Gly Lys Ile Gly Asn Met Arg Gln Ala His Cys Asn Ile Ser
290                 295                 300

Arg Ala Lys Trp Asn Asn Thr Leu Lys Gln Ile Ala Ser Lys Leu Arg
305                 310                 315                 320

Glu Gln Phe Gly Asn Asn Lys Thr Ile Ile Phe Lys Gln Ser Ser Gly
                325                 330                 335

Gly Asp Pro Glu Ile Val Thr His Ser Phe Asn Cys Gly Gly Glu Phe
            340                 345                 350

Phe Tyr Cys Asn Ser Thr Gln Leu Phe Asn Ser Thr Trp Phe Asn Ser
            355                 360                 365

Thr Trp Ser Thr Glu Gly Ser Asn Asn Thr Glu Gly Ser Asp Thr Ile
370                 375                 380

Thr Leu Pro Cys Arg Ile Lys Gln Ile Ile Asn Met Trp Gln Lys Val
385                 390                 395                 400

Gly Lys Ala Met Tyr Ala Pro Pro Ile Ser Gly Gln Ile Arg Cys Ser
                405                 410                 415

Ser Asn Ile Thr Gly Leu Leu Leu Thr Arg Asp Gly Gly Asn Ser Asn
                420                 425                 430

Asn Glu Ser Glu Ile Phe Arg Pro Gly Gly Gly Asp Met Arg Asp Asn
            435                 440                 445

Trp Arg Ser Glu Leu Tyr Lys Tyr Lys Val Val Lys Ile Glu Pro Leu
450                 455                 460
```

```
Gly Val Ala Pro Thr Lys Ala Lys Arg Arg Val Gln Arg Glu Lys
465                 470                 475                 480

Arg
```

<210> SEQ ID NO 3
<211> LENGTH: 710
<212> TYPE: PRT
<213> ORGANISM: Artificial sequence
<220> FEATURE:
<223> OTHER INFORMATION: CD4-[2-helix-2]-7B2 DVR heavy chain

<400> SEQUENCE: 3

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
            195                 200                 205

Gly Gly Gly Gly Ser Gly Gly Gly Ser Leu Glu Ala Glu Ala Ala
210                 215                 220

Ala Lys Glu Ala Ala Ala Lys Glu Ala Ala Ala Lys Glu Ala Ala Ala
225                 230                 235                 240

Lys Ala Leu Glu Gly Gly Gly Ser Gly Gly Gly Ser Gln Val
                245                 250                 255

Gln Leu Val Gln Ser Gly Gly Gly Val Phe Lys Pro Gly Gly Ser Leu
            260                 265                 270

Arg Leu Ser Cys Glu Ala Ser Gly Phe Thr Phe Thr Glu Tyr Tyr Met
275                 280                 285

Thr Trp Val Arg Gln Ala Pro Gly Lys Gly Leu Glu Trp Leu Ala Tyr
290                 295                 300

Ile Ser Lys Asn Gly Glu Tyr Ser Lys Tyr Ser Pro Ser Ser Asn Gly
305                 310                 315                 320

Arg Phe Thr Ile Ser Arg Asp Asn Ala Lys Asn Ser Val Phe Leu Gln
                325                 330                 335

Leu Asp Arg Leu Ser Ala Asp Asp Thr Ala Val Tyr Tyr Cys Ala Arg
```

Ala Asp Gly Leu Thr Tyr Phe Ser Glu Leu Leu Gln Tyr Ile Phe Asp
                340                 345                 350
Leu Trp Gly Gln Gly Ala Arg Val Thr Val Ser Ser Ala Ser Thr Lys
            355                 360                 365
Gly Pro Ser Val Phe Pro Leu Ala Pro Ser Ser Lys Ser Thr Ser Gly
370                 375                 380
Gly Thr Ala Ala Leu Gly Cys Leu Val Lys Asp Tyr Phe Pro Glu Pro
385                 390                 395                 400
Val Thr Val Ser Trp Asn Ser Gly Ala Leu Thr Ser Gly Val His Thr
            405                 410                 415
Phe Pro Ala Val Leu Gln Ser Ser Gly Leu Tyr Ser Leu Ser Ser Val
                420                 425                 430
Val Thr Val Pro Ser Ser Leu Gly Thr Gln Thr Tyr Ile Cys Asn
            435                 440                 445
Val Asn His Lys Pro Ser Asn Thr Lys Val Asp Lys Lys Val Glu Pro
                450                 455                 460
Lys Ser Cys Asp Lys Thr His Thr Cys Pro Pro Cys Pro Ala Pro Glu
465                 470                 475                 480
Leu Leu Gly Gly Pro Ser Val Phe Leu Phe Pro Pro Lys Pro Lys Asp
            485                 490                 495
Thr Leu Met Ile Ser Arg Thr Pro Glu Val Thr Cys Val Val Val Asp
                500                 505                 510
Val Ser His Glu Asp Pro Glu Val Lys Phe Asn Trp Tyr Val Asp Gly
            515                 520                 525
Val Glu Val His Asn Ala Lys Thr Lys Pro Arg Glu Glu Gln Tyr Asn
530                 535                 540
Ser Thr Tyr Arg Val Val Ser Val Leu Thr Val Leu His Gln Asp Trp
            545                 550                 555
Leu Asn Gly Lys Glu Tyr Lys Cys Lys Val Ser Asn Lys Ala Leu Pro
                560                 565                 570
Ala Pro Ile Glu Lys Thr Ile Ser Lys Ala Lys Gly Gln Pro Arg Glu
            575                 580                 585
Pro Gln Val Tyr Thr Leu Pro Pro Ser Arg Asp Glu Leu Thr Lys Asn
590                 595                 600
Gln Val Ser Leu Thr Cys Leu Val Lys Gly Phe Tyr Pro Ser Asp Ile
            605                 610                 615                 620
Ala Val Glu Trp Glu Ser Asn Gly Gln Pro Glu Asn Asn Tyr Lys Thr
                625                 630                 635
Thr Pro Pro Val Leu Asp Ser Asp Gly Ser Phe Phe Leu Tyr Ser Lys
            640                 645                 650
Leu Thr Val Asp Lys Ser Arg Trp Gln Gln Gly Asn Val Phe Ser Cys
                655                 660                 665
Ser Val Met His Glu Ala Leu His Asn His Tyr Thr Gln Lys Ser Leu
            670                 675                 680
Ser Leu Ser Pro Gly Lys
685                 690

<210> SEQ ID NO 4
<211> LENGTH: 690
<212> TYPE: PRT
<213> ORGANISM: Artificial sequence
<220> FEATURE:
<223> OTHER INFORMATION: CD4-[helix]x4-7B2 DVR heavy chain

<400> SEQUENCE: 4

```
Met Asn Arg Gly Val Pro Phe Arg His Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
                35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65              70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
                115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
                195                 200                 205

Leu Glu Ala Glu Ala Ala Lys Glu Ala Ala Lys Glu Ala Ala
    210                 215                 220

Ala Lys Glu Ala Ala Lys Ala Leu Glu Gln Val Gln Leu Val Gln
225                 230                 235                 240

Ser Gly Gly Gly Val Phe Lys Pro Gly Gly Ser Leu Arg Leu Ser Cys
                245                 250                 255

Glu Ala Ser Gly Phe Thr Phe Thr Glu Tyr Tyr Met Thr Trp Val Arg
                260                 265                 270

Gln Ala Pro Gly Lys Gly Leu Glu Trp Leu Ala Tyr Ile Ser Lys Asn
                275                 280                 285

Gly Glu Tyr Ser Lys Tyr Ser Pro Ser Ser Asn Gly Arg Phe Thr Ile
    290                 295                 300

Ser Arg Asp Asn Ala Lys Asn Ser Val Phe Leu Gln Leu Asp Arg Leu
305                 310                 315                 320

Ser Ala Asp Asp Thr Ala Val Tyr Tyr Cys Ala Arg Ala Asp Gly Leu
                325                 330                 335

Thr Tyr Phe Ser Glu Leu Leu Gln Tyr Ile Phe Asp Leu Trp Gly Gln
                340                 345                 350

Gly Ala Arg Val Thr Val Ser Ser Ala Ser Thr Lys Gly Pro Ser Val
                355                 360                 365

Phe Pro Leu Ala Pro Ser Ser Lys Ser Thr Ser Gly Gly Thr Ala Ala
    370                 375                 380

Leu Gly Cys Leu Val Lys Asp Tyr Phe Pro Glu Pro Val Thr Val Ser
385                 390                 395                 400

Trp Asn Ser Gly Ala Leu Thr Ser Gly Val His Thr Phe Pro Ala Val
                405                 410                 415
```

Leu Gln Ser Ser Gly Leu Tyr Ser Leu Ser Ser Val Val Thr Val Pro
                420                 425                 430

Ser Ser Ser Leu Gly Thr Gln Thr Tyr Ile Cys Asn Val Asn His Lys
                435                 440                 445

Pro Ser Asn Thr Lys Val Asp Lys Val Glu Pro Lys Ser Cys Asp
450                 455                 460

Lys Thr His Thr Cys Pro Pro Cys Pro Ala Pro Glu Leu Leu Gly Gly
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
                500                 505                 510

Asp Pro Glu Val Lys Phe Asn Trp Tyr Val Asp Gly Val Glu Val His
                515                 520                 525

Asn Ala Lys Thr Lys Pro Arg Glu Glu Gln Tyr Asn Ser Thr Tyr Arg
530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Pro Ala Pro Ile Glu
                565                 570                 575

Lys Thr Ile Ser Lys Ala Lys Gly Gln Pro Arg Glu Pro Gln Val Tyr
                580                 585                 590

Thr Leu Pro Pro Ser Arg Asp Glu Leu Thr Lys Asn Gln Val Ser Leu
                595                 600                 605

Thr Cys Leu Val Lys Gly Phe Tyr Pro Ser Asp Ile Ala Val Glu Trp
610                 615                 620

Glu Ser Asn Gly Gln Pro Glu Asn Asn Tyr Lys Thr Thr Pro Pro Val
625                 630                 635                 640

Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
                660                 665                 670

Glu Ala Leu His Asn His Tyr Thr Gln Lys Ser Leu Ser Leu Ser Pro
                675                 680                 685

Gly Lys
    690

<210> SEQ ID NO 5
<211> LENGTH: 502
<212> TYPE: PRT
<213> ORGANISM: Artificial sequence
<220> FEATURE:
<223> OTHER INFORMATION: CD4-[2-helix-2]-7B2 DVR light chain

<400> SEQUENCE: 5

Met Thr Ser Thr Leu Pro Phe Ser Pro Gln Val Ser Thr Pro Arg Ser
1               5                   10                  15

Lys Phe Lys Arg Ile Ser Ser Glu Phe Ala Ala Thr Met Asn Arg Gly
                20                  25                  30

Val Pro Phe Arg His Leu Leu Leu Val Leu Gln Leu Ala Leu Leu Pro
                35                  40                  45

Ala Ala Thr Gln Gly Lys Lys Val Val Leu Gly Lys Lys Gly Asp Thr
50                  55                  60

Val Glu Leu Thr Cys Thr Ala Ser Gln Lys Lys Ser Ile Gln Phe His
65                  70                  75                  80

```
Trp Lys Asn Ser Asn Gln Ile Lys Ile Leu Gly Asn Gln Gly Ser Phe
                85                  90                  95
Leu Thr Lys Gly Pro Ser Lys Leu Asn Asp Arg Ala Asp Ser Arg Arg
            100                 105                 110
Ser Leu Trp Asp Gln Gly Asn Phe Pro Leu Ile Ile Lys Asn Leu Lys
        115                 120                 125
Ile Glu Asp Ser Asp Thr Tyr Ile Cys Glu Val Glu Asp Gln Lys Glu
    130                 135                 140
Glu Val Gln Leu Leu Val Phe Gly Leu Thr Ala Asn Ser Asp Thr His
145                 150                 155                 160
Leu Leu Gln Gly Gln Ser Leu Thr Leu Thr Leu Glu Ser Pro Pro Gly
                165                 170                 175
Ser Ser Pro Ser Val Gln Cys Arg Ser Pro Arg Gly Lys Asn Ile Gln
            180                 185                 190
Gly Gly Lys Thr Leu Ser Val Ser Gln Leu Glu Leu Gln Asp Ser Gly
        195                 200                 205
Thr Trp Thr Cys Thr Val Leu Gln Asn Gln Lys Lys Val Glu Phe Lys
    210                 215                 220
Ile Asp Ile Val Val Leu Ala Phe Gln Lys Ala Ser Gly Gly Gly Gly
225                 230                 235                 240
Ser Gly Gly Gly Gly Ser Leu Glu Ala Glu Ala Ala Lys Glu Ala
                245                 250                 255
Ala Ala Lys Glu Ala Ala Ala Lys Glu Ala Ala Ala Lys Ala Leu Glu
                260                 265                 270
Gly Gly Gly Gly Ser Gly Gly Gly Ser Asp Ile Val Met Thr Gln
        275                 280                 285
Ser Pro Asp Ser Leu Ala Val Ser Pro Gly Glu Arg Ala Thr Ile His
    290                 295                 300
Cys Lys Ser Ser Gln Thr Leu Leu Tyr Ser Ser Asn Asn Arg His Ser
305                 310                 315                 320
Ile Ala Trp Tyr Gln Gln Arg Pro Gly Gln Pro Pro Lys Leu Leu Leu
                325                 330                 335
Tyr Trp Ala Ser Met Arg Leu Ser Gly Val Pro Asp Arg Phe Ser Gly
            340                 345                 350
Ser Gly Ser Gly Thr Asp Phe Thr Leu Thr Ile Asn Asn Leu Gln Ala
        355                 360                 365
Glu Asp Val Ala Ile Tyr Tyr Cys His Gln Tyr Ser Ser His Pro Pro
    370                 375                 380
Thr Phe Gly His Gly Thr Arg Val Glu Leu Arg Arg Thr Val Ala Ala
385                 390                 395                 400
Pro Ser Val Phe Ile Phe Pro Pro Ser Asp Glu Gln Leu Lys Ser Gly
                405                 410                 415
Thr Ala Ser Val Val Cys Leu Leu Asn Asn Phe Tyr Pro Arg Glu Ala
            420                 425                 430
Lys Val Gln Trp Lys Val Asp Asn Ala Leu Gln Ser Gly Asn Ser Gln
        435                 440                 445
Glu Ser Val Thr Glu Gln Asp Ser Lys Asp Ser Thr Tyr Ser Leu Ser
    450                 455                 460
Ser Thr Leu Thr Leu Ser Lys Ala Asp Tyr Glu Lys His Lys Val Tyr
465                 470                 475                 480
Ala Cys Glu Val Thr His Gln Gly Leu Ser Ser Pro Val Thr Lys Ser
                485                 490                 495
```

-continued

Phe Asn Arg Gly Glu Cys
                    500

<210> SEQ ID NO 6
<211> LENGTH: 482
<212> TYPE: PRT
<213> ORGANISM: Artificial sequence
<220> FEATURE:
<223> OTHER INFORMATION: CD4-[helix]x4-7B2 DVR light chain

<400> SEQUENCE: 6

Met Thr Ser Thr Leu Pro Phe Ser Pro Gln Val Ser Thr Pro Arg Ser
1               5                   10                  15

Lys Phe Lys Arg Ile Ser Ser Glu Phe Ala Ala Thr Met Asn Arg Gly
            20                  25                  30

Val Pro Phe Arg His Leu Leu Leu Val Leu Gln Leu Ala Leu Leu Pro
        35                  40                  45

Ala Ala Thr Gln Gly Lys Lys Val Leu Gly Lys Lys Gly Asp Thr
    50                  55                  60

Val Glu Leu Thr Cys Thr Ala Ser Gln Lys Lys Ser Ile Gln Phe His
65                  70                  75                  80

Trp Lys Asn Ser Asn Gln Ile Lys Ile Leu Gly Asn Gln Gly Ser Phe
                85                  90                  95

Leu Thr Lys Gly Pro Ser Lys Leu Asn Asp Arg Ala Asp Ser Arg Arg
            100                 105                 110

Ser Leu Trp Asp Gln Gly Asn Phe Pro Leu Ile Ile Lys Asn Leu Lys
        115                 120                 125

Ile Glu Asp Ser Asp Thr Tyr Ile Cys Glu Val Glu Asp Gln Lys Glu
130                 135                 140

Glu Val Gln Leu Leu Val Phe Gly Leu Thr Ala Asn Ser Asp Thr His
145                 150                 155                 160

Leu Leu Gln Gly Gln Ser Leu Thr Leu Thr Leu Glu Ser Pro Pro Gly
                165                 170                 175

Ser Ser Pro Ser Val Gln Cys Arg Ser Pro Arg Gly Lys Asn Ile Gln
            180                 185                 190

Gly Gly Lys Thr Leu Ser Val Ser Gln Leu Glu Leu Gln Asp Ser Gly
        195                 200                 205

Thr Trp Thr Cys Thr Val Leu Gln Asn Gln Lys Lys Val Glu Phe Lys
210                 215                 220

Ile Asp Ile Val Val Leu Ala Phe Gln Lys Ala Ser Leu Glu Ala Glu
225                 230                 235                 240

Ala Ala Ala Lys Glu Ala Ala Ala Lys Glu Ala Ala Ala Lys Glu Ala
                245                 250                 255

Ala Ala Lys Ala Leu Glu Asp Ile Val Met Thr Gln Ser Pro Asp Ser
            260                 265                 270

Leu Ala Val Ser Pro Gly Glu Arg Ala Thr Ile His Cys Lys Ser Ser
        275                 280                 285

Gln Thr Leu Leu Tyr Ser Ser Asn Asn Arg His Ser Ile Ala Trp Tyr
290                 295                 300

Gln Gln Arg Pro Gly Gln Pro Pro Lys Leu Leu Leu Tyr Trp Ala Ser
305                 310                 315                 320

Met Arg Leu Ser Gly Val Pro Asp Arg Phe Ser Gly Ser Gly Ser Gly
                325                 330                 335

Thr Asp Phe Thr Leu Thr Ile Asn Asn Leu Gln Ala Glu Asp Val Ala
            340                 345                 350

```
Ile Tyr Tyr Cys His Gln Tyr Ser Ser His Pro Pro Thr Phe Gly His
            355                 360                 365

Gly Thr Arg Val Glu Leu Arg Arg Thr Val Ala Ala Pro Ser Val Phe
370                 375                 380

Ile Phe Pro Pro Ser Asp Glu Gln Leu Lys Ser Gly Thr Ala Ser Val
385                 390                 395                 400

Val Cys Leu Leu Asn Asn Phe Tyr Pro Arg Glu Ala Lys Val Gln Trp
            405                 410                 415

Lys Val Asp Asn Ala Leu Gln Ser Gly Asn Ser Gln Glu Ser Val Thr
            420                 425                 430

Glu Gln Asp Ser Lys Asp Ser Thr Tyr Ser Leu Ser Ser Thr Leu Thr
            435                 440                 445

Leu Ser Lys Ala Asp Tyr Glu Lys His Lys Val Tyr Ala Cys Glu Val
    450                 455                 460

Thr His Gln Gly Leu Ser Ser Pro Val Thr Lys Ser Phe Asn Arg Gly
465                 470                 475                 480

Glu Cys
```

<210> SEQ ID NO 7
<211> LENGTH: 240
<212> TYPE: PRT
<213> ORGANISM: Artificial sequence
<220> FEATURE:
<223> OTHER INFORMATION: Monoclonal antibody 7B2 light chain

<400> SEQUENCE: 7

```
Met Glu Thr Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
            20                  25                  30

Val Ser Pro Gly Glu Arg Ala Thr Ile His Cys Lys Ser Ser Gln Thr
        35                  40                  45

Leu Leu Tyr Ser Ser Asn Asn Arg His Ser Ile Ala Trp Tyr Gln Gln
    50                  55                  60

Arg Pro Gly Gln Pro Pro Lys Leu Leu Leu Tyr Trp Ala Ser Met Arg
65                  70                  75                  80

Leu Ser Gly Val Pro Asp Arg Phe Ser Gly Ser Gly Ser Gly Thr Asp
                85                  90                  95

Phe Thr Leu Thr Ile Asn Asn Leu Gln Ala Glu Asp Val Ala Ile Tyr
            100                 105                 110

Tyr Cys His Gln Tyr Ser Ser His Pro Pro Thr Phe Gly His Gly Thr
        115                 120                 125

Arg Val Glu Leu Arg Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
```

<210> SEQ ID NO 8
<211> LENGTH: 475
<212> TYPE: PRT
<213> ORGANISM: Artificial sequence
<220> FEATURE:
<223> OTHER INFORMATION: Monoclonal antibody 7B2 heavy chain

<400> SEQUENCE: 8

| | | | | | | | | | | | | | | | |
|---|---|---|---|---|---|---|---|---|---|---|---|---|---|---|---|
| Met | Asp | Trp | Thr | Trp | Arg | Val | Leu | Phe | Leu | Val | Ala | Ala | Ala | Thr | Gly |
| 1 | | | | 5 | | | | | 10 | | | | | 15 | |
| Ala | His | Ser | Gln | Val | Gln | Leu | Val | Gln | Ser | Gly | Gly | Gly | Val | Phe | Lys |
| | | | 20 | | | | | 25 | | | | | 30 | | |
| Pro | Gly | Gly | Ser | Leu | Arg | Leu | Ser | Cys | Glu | Ala | Ser | Gly | Phe | Thr | Phe |
| | | | 35 | | | | | 40 | | | | | 45 | | |
| Thr | Glu | Tyr | Tyr | Met | Thr | Trp | Val | Arg | Gln | Ala | Pro | Gly | Lys | Gly | Leu |
| | 50 | | | | | 55 | | | | | 60 | | | | |
| Glu | Trp | Leu | Ala | Tyr | Ile | Ser | Lys | Asn | Gly | Tyr | Ser | Lys | Tyr | Ser |
| 65 | | | | | 70 | | | | | 75 | | | | | 80 |
| Pro | Ser | Ser | Asn | Gly | Arg | Phe | Thr | Ile | Ser | Arg | Asp | Asn | Ala | Lys | Asn |
| | | | | 85 | | | | | 90 | | | | | 95 | |
| Ser | Val | Phe | Leu | Gln | Leu | Asp | Arg | Leu | Ser | Ala | Asp | Asp | Thr | Ala | Val |
| | | | 100 | | | | | 105 | | | | | 110 | | |
| Tyr | Tyr | Cys | Ala | Arg | Ala | Asp | Gly | Leu | Thr | Tyr | Phe | Ser | Glu | Leu | Leu |
| | | | 115 | | | | | 120 | | | | | 125 | | |
| Gln | Tyr | Ile | Phe | Asp | Leu | Trp | Gly | Gln | Gly | Ala | Arg | Val | Thr | Val | Ser |
| | 130 | | | | | 135 | | | | | 140 | | | | |
| Ser | Ala | Ser | Thr | Lys | Gly | Pro | Ser | Val | Phe | Pro | Leu | Ala | Pro | Ser | Ser |
| 145 | | | | | 150 | | | | | 155 | | | | | 160 |
| Lys | Ser | Thr | Ser | Gly | Gly | Thr | Ala | Ala | Leu | Gly | Cys | Leu | Val | Lys | Asp |
| | | | | 165 | | | | | 170 | | | | | 175 | |
| Tyr | Phe | Pro | Glu | Pro | Val | Thr | Val | Ser | Trp | Asn | Ser | Gly | Ala | Leu | Thr |
| | | | 180 | | | | | 185 | | | | | 190 | | |
| Ser | Gly | Val | His | Thr | Phe | Pro | Ala | Val | Leu | Gln | Ser | Ser | Gly | Leu | Tyr |
| | | | 195 | | | | | 200 | | | | | 205 | | |
| Ser | Leu | Ser | Ser | Val | Val | Thr | Val | Pro | Ser | Ser | Ser | Leu | Gly | Thr | Gln |
| | 210 | | | | | 215 | | | | | 220 | | | | |
| Thr | Tyr | Ile | Cys | Asn | Val | Asn | His | Lys | Pro | Ser | Asn | Thr | Lys | Val | Asp |
| 225 | | | | | 230 | | | | | 235 | | | | | 240 |
| Lys | Arg | Val | Glu | Pro | Lys | Ser | Cys | Asp | Lys | Thr | His | Thr | Cys | Pro | Pro |
| | | | | 245 | | | | | 250 | | | | | 255 | |
| Cys | Pro | Ala | Pro | Glu | Leu | Leu | Gly | Gly | Pro | Ser | Val | Phe | Leu | Phe | Pro |
| | | | 260 | | | | | 265 | | | | | 270 | | |
| Pro | Lys | Pro | Lys | Asp | Thr | Leu | Met | Ile | Ser | Arg | Thr | Pro | Glu | Val | Thr |
| | | | 275 | | | | | 280 | | | | | 285 | | |
| Cys | Val | Val | Val | Asp | Val | Ser | His | Glu | Asp | Pro | Glu | Val | Lys | Phe | Asn |
| | 290 | | | | | 295 | | | | | 300 | | | | |
| Trp | Tyr | Val | Asp | Gly | Val | Glu | Val | His | Asn | Ala | Lys | Thr | Lys | Pro | Arg |
| 305 | | | | | 310 | | | | | 315 | | | | | 320 |
| Glu | Glu | Gln | Tyr | Asn | Ser | Thr | Tyr | Arg | Val | Val | Ser | Val | Leu | Thr | Val |
| | | | | 325 | | | | | 330 | | | | | 335 | |
| Leu | His | Gln | Asp | Trp | Leu | Asn | Gly | Lys | Glu | Tyr | Lys | Cys | Lys | Val | Ser |
| | | | 340 | | | | | 345 | | | | | 350 | | |
| Asn | Lys | Ala | Leu | Pro | Ala | Pro | Ile | Glu | Lys | Thr | Ile | Ser | Lys | Ala | Lys |

-continued

```
                355                 360                 365
Gly Gln Pro Arg Glu Pro Gln Val Tyr Thr Leu Pro Pro Ser Arg Glu
        370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 9
<211> LENGTH: 26
<212> TYPE: PRT
<213> ORGANISM: Artificial sequence
<220> FEATURE:
<223> OTHER INFORMATION: Helical linker

<400> SEQUENCE: 9

Leu Glu Ala Glu Ala Ala Ala Lys Glu Ala Ala Lys Glu Ala Ala
1               5                   10                  15

Ala Lys Glu Ala Ala Ala Lys Ala Leu Glu
            20                  25

<210> SEQ ID NO 10
<211> LENGTH: 46
<212> TYPE: PRT
<213> ORGANISM: Artificial sequence
<220> FEATURE:
<223> OTHER INFORMATION: 2-Helix-2 linker

<400> SEQUENCE: 10

Gly Gly Gly Gly Ser Gly Gly Gly Ser Leu Glu Ala Glu Ala Ala
1               5                   10                  15

Ala Lys Glu Ala Ala Lys Glu Ala Ala Ala Lys Glu Ala Ala Ala
            20                  25                  30

Lys Ala Leu Glu Gly Gly Gly Ser Gly Gly Gly Ser
            35                  40                  45
```